US012714371B2

(12) United States Patent
Neihouser et al.

(10) Patent No.: US 12,714,371 B2
(45) Date of Patent: Aug. 25, 2026

(54) COMMUNICATION TOOL AND UWB-EQUIPPED PATIENT DEVICES

(71) Applicant: Stryker Corporation, Kalamazoo, MI (US)

(72) Inventors: Kirby M. Neihouser, Portage, MI (US); Jerald A. Trepanier, Augusta, MI (US); Madhu Sandeep Thota, Portage, MI (US); Celso Henrique Farnese Pires Pereira, Portage, MI (US); Krishna Sandeep Bhimavarapu, Kalamazoo, MI (US); Christopher P. Alvarez, Kalamazoo, MI (US); Nicholas S. Brajak, Portage, MI (US); Michael W. Graves, Paw Paw, MI (US); Madhu Thomas, London (CA); Sujay Sukumaran, Portage, MI (US)

(73) Assignee: Stryker Corporation, Portage, MI (US)

( * ) Notice: Subject to any disclaimer, the term of this patent is extended or adjusted under 35 U.S.C. 154(b) by 280 days.

(21) Appl. No.: 18/519,853

(22) Filed: Nov. 27, 2023

(65) Prior Publication Data

US 2024/0172997 A1 May 30, 2024

Related U.S. Application Data

(60) Provisional application No. 63/428,075, filed on Nov. 27, 2022.

(51) Int. Cl.
*G08B 21/00* (2006.01)
*A61B 5/00* (2006.01)
*A61B 5/11* (2006.01)

(52) U.S. Cl.
CPC ............ *A61B 5/6887* (2013.01); *A61B 5/002* (2013.01); *A61B 5/1115* (2013.01); *A61B 5/742* (2013.01)

(58) Field of Classification Search
CPC ..... A61B 5/6887; A61B 5/002; A61B 5/1115; A61B 5/742; A61B 5/6891
See application file for complete search history.

(56) References Cited

U.S. PATENT DOCUMENTS 7,242,306 B2 7/2007 Wildman et al.
7,570,152 B2 8/2009 Smith et al.
(Continued)

FOREIGN PATENT DOCUMENTS

WO 2017/151683 A1 9/2017
WO 2020/264140 A1 12/2020
(Continued)

*Primary Examiner* — Toan N Pham
(74) *Attorney, Agent, or Firm* — Gardner, Linn, Burkhart & Ondersma LLP

(57) ABSTRACT

A portable tool for communicating with an ultra-wideband (UWB) equipped patient support apparatus and/or a UWB-equipped locator unit. The tool may include a housing, a transceiver for communicating with a computer, a first (UWB) transceiver adapted to communicate with a second UWB transceiver, and a controller. The controller may be adapted to use the first UWB transceiver to obtain an identifier from the second UWB transceiver, and to determine whether the second UWB transceiver is positioned onboard a patient support apparatus or onboard a locator unit based on its identifier. If the second UWB transceiver is positioned onboard the patient support apparatus, the tool may determine a specific location of the second UWB transceiver onboard the patient support apparatus. The tool may alternatively be embodied in a software application adapted to be executed on a smart phone and/or personal computer.

20 Claims, 9 Drawing Sheets

(56) References Cited

U.S. PATENT DOCUMENTS 8,334,777 B2 12/2012 Wilson et al.
8,334,779 B2 12/2012 Zerhusen et al.
8,552,903 B2 10/2013 Julian et al.
8,756,078 B2 6/2014 Collins, Jr. et al.
8,786,402 B2 7/2014 Barnes
9,320,662 B2 4/2016 Hayes et al.
9,427,365 B2 8/2016 Richards et al.
9,554,286 B2 1/2017 Ghabra et al.
9,569,591 B2 2/2017 Vanderpohl, III
9,571,985 B2 2/2017 Borrazzi et al.
9,788,151 B2 10/2017 Duan et al.
9,937,090 B2* 4/2018 Hayes .................... G16H 40/20
9,999,375 B2* 6/2018 Hayes .................. A61B 5/6892
10,064,012 B1 8/2018 Boston et al.
10,258,538 B2 4/2019 Barta et al.
10,474,808 B2 11/2019 Huster
10,486,646 B2 11/2019 Ledvina et al.
10,608,699 B2 3/2020 Nabki et al.
10,759,389 B2 9/2020 Ledvina et al.
10,811,136 B2 10/2020 Bhimavarapu et al.
10,846,961 B2 11/2020 de Perthuis et al.
11,019,195 B2 5/2021 Ledvina et al.
11,026,607 B2 6/2021 Martin et al.
11,082,809 B1 8/2021 Burowski et al.
11,153,810 B2 10/2021 Yoon et al.
11,289,194 B1 3/2022 Pipher et al.
11,301,651 B2 4/2022 Studerus et al.
11,343,645 B2 5/2022 Yoon et al.
11,400,889 B2 8/2022 Parthasarathi et al.
11,610,671 B2 3/2023 Hochworter
11,638,233 B2 4/2023 Shin et al.
11,699,517 B2* 7/2023 Receveur ............. H04B 17/318 705/2
12,154,685 B2* 11/2024 Durlach ............... A61B 5/4824
12,165,767 B2* 12/2024 Tallent ................... G16H 40/40
2008/0312971 A2 12/2008 Rowsow et al.
2011/0208541 A1 8/2011 Wilson et al.
2014/0297327 A1 10/2014 Heil et al.
2014/0320290 A1 10/2014 Reeder et al.
2016/0140307 A1 5/2016 Brosnan et al.
2017/0287316 A1 10/2017 Wildman et al.
2017/0340498 A1 11/2017 Tessmer et al.
2018/0028824 A1 2/2018 Pivonka et al.
2019/0008708 A1* 1/2019 Moreno ................ G06F 3/0489
2019/0198168 A1* 6/2019 Lee ........................ G16H 10/60
2021/0014677 A1 1/2021 Han et al.
2021/0065885 A1 3/2021 Receveur et al.
2021/0266710 A1 8/2021 Martin et al.
2021/0360366 A1 11/2021 Bailey et al.
2021/0400439 A1 12/2021 Troester et al.
2022/0053292 A1 2/2022 Hoff et al.
2022/0137204 A1 5/2022 Nguyen et al.
2022/0139133 A1 5/2022 Schober et al.
2022/0208368 A1 6/2022 Niehouser et al.
2022/0208372 A1 6/2022 Bodurka et al.
2022/0241124 A1 8/2022 Bhimavarapu et al.
2022/0287897 A1 9/2022 Bhimavarapu et al.
2023/0337941 A1 10/2023 Pereira et al.

FOREIGN PATENT DOCUMENTS

WO 2021/228946 A1 11/2021
WO 2021/236649 A1 11/2021
WO 2022/086515 A1 4/2022
WO 2022/232207 A1 11/2022

* cited by examiner

| UWB Transceiver | Product | Make | Model | Internal Location | Signal Strength | Lar Ranging Sessions | Errors | Distance |
|---|---|---|---|---|---|---|---|---|
| QZT433 | Bed | Stryker | Procuity | Left Head End | -50db | AFR122 | 3440, 0001 | 2.5 meters |
| QZT432 | Bed | Stryker | Procuity | Left Foot End | -55db | AFR122 | 0002 | 1.8 meters |
| QZT431 | Bed | Stryker | Procuity | Right Head End | -56db | AFR122 | None | 2.2 meters |
| QZT430 | Bed | Stryker | Procuity | Right Foot End | -54db | AFR122 | None | 2.2 meters |
| AFR122 | Locator | Stryker | Secure Connect | Center | -60db | QZT433, QZT432 QZT432, QZT430 | None | 3.3 meters |
| EDX101 | Exercise Device | Stryker | 432 | Center | -54db | QZT433, QZT432, QZT432, QZT430 | None | 2.4 meters |
| TMM202 | Temperature Management | Stryker | Altrix | Center | -62db | QZT433, QZT432, QZT432, QZT430 | None | 4.5 meters |

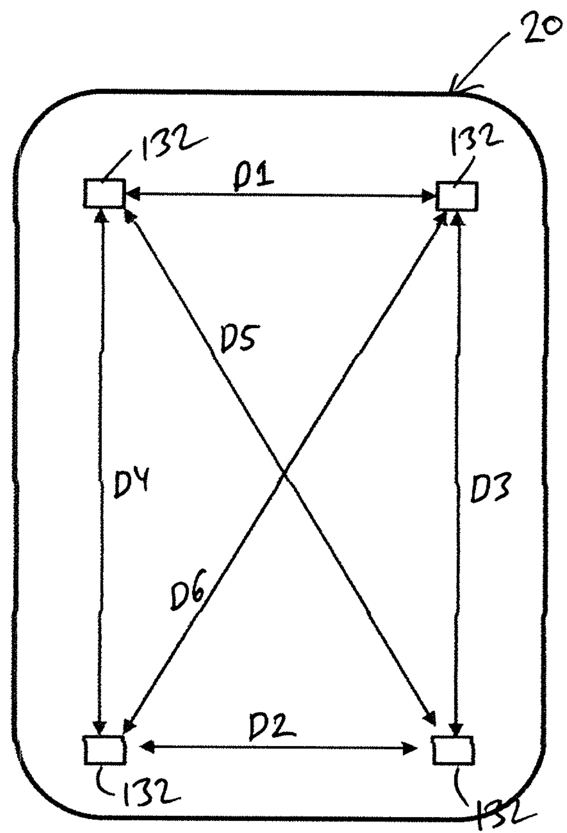
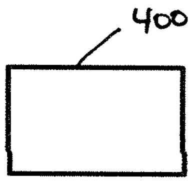
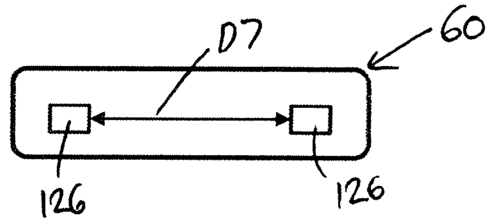
FIG. 9

COMMUNICATION TOOL AND UWB-EQUIPPED PATIENT DEVICES

CROSS-REFERENCE TO RELATED APPLICATIONS

This application claims priority to U.S. provisional patent application Ser. No. 63/428,075 filed Nov. 27, 2022, by inventors Kirby Neihouser et al. and entitled COMMUNICATION TOOL FOR UWB EQUIPPED PATIENT DEVICES, the complete disclosure of which is incorporated herein by reference.

BACKGROUND

The present disclosure relates to patient support apparatuses, such as beds, cots, stretchers, recliners, or the like, and more particularly to a tool for communicating with patient support apparatuses that include one or more ultra-wideband transceivers incorporated into them.

In some situations, hospital beds communicate with the nurse call system and/or the room devices wirelessly using a wall unit as a communication intermediary. The wall unit may include one or more ultra-wideband transceivers integrated into it that are adapted to communicate with one or more ultra-wideband transceivers that are incorporated into the patient support apparatus.

SUMMARY

According to various embodiments, the present disclosure provides an improved tool for easily communicating with patient support apparatuses, fixed locator units, and/or other UWB devices that include one or more ultra-wideband (UWB) transceivers integrated into them. The tool enables a technician or other authorized individual to configure, test, debug, and/or gather data regarding the UWB transceivers onboard the UWB device (e.g. patient support apparatuses, wall units, or other UWB devices). If there is more than one UWB transceiver built into the UWB device, the tool may automatically identify the locations of the multiple UWB devices so that the technician can more easily distinguish one UWB transceiver from another. The tool may also, or additionally, identify which device (e.g. patient support apparatus, wall unit, or other type of device) the UWB transceiver is integrated into so that the technician knows which device to inspect if any errors are occurring with a particular UWB transceiver. The tool may be used to transmit and/or install a software update on the UWB device. The tool may also command the device to take one or more distance measurements of using their UWB transceivers, compare them to known distances, and determine if an error may exist in one or more of the UWB transceivers. These and other features of the present disclosure will be apparent to one of ordinary skill in light of the accompanying drawings and the following written description.

According to a first embodiment of the present disclosure, a portable communication tool is provided for communicating with a patient support apparatus. The tool includes a housing, a transceiver for communicating with a computer, a first ultra-wideband (UWB) transceiver adapted to communicate with a second UWB transceiver incorporated into the patient support apparatus, and a controller. The controller is adapted to perform the following: (a) use the first UWB transceiver to obtain an identifier from the second UWB transceiver onboard the patient support apparatus; (b) determine a location of the second UWB transceiver onboard the patient support apparatus based on the identifier; and (c) forward the identifier and the location of the second UWB transceiver to the transceiver for display on the computer.

According to another embodiment of the present disclosure, a portable communication tool is provided for communicating with at least one of a patient support apparatus or locator unit mounted at a fixed location within a healthcare facility. The tool includes a housing, a transceiver for communicating with a computer, a first ultra-wideband (UWB) transceiver adapted to communicate with a second UWB transceiver, and a controller. The controller is adapted to perform the following: (a) use the first UWB transceiver to obtain an identifier from the second UWB transceiver; (b) determine whether the second UWB transceiver is onboard the patient support apparatus or onboard the locator unit based on the identifier; and (c) forward data indicating whether the second UWB transceiver is onboard the patient support apparatus or onboard the locator unit to the transceiver for display on the computer.

According to other aspects of the present disclosure, the controller may be further adapted to determine a distance between the first UWB transceiver and the second UWB transceiver by using the first UWB transceiver to range with the second UWB transceiver using ultra-wideband.

In some aspects, the controller is further adapted to forward the distance to the transceiver for display on the computer.

The controller, in some aspects, is adapted to measure a quality of UWB signals sent by the second UWB transceiver and detected by the first UWB transceiver.

In some aspects, the controller is further adapted to forward the measurement of quality to the transceiver for display on the computer.

The controller, in some aspects, is further adapted to use the first UWB transceiver to retrieve error codes from the second UWB transceiver and to forward the error codes to the transceiver for display on the computer.

In some aspects, the controller is further adapted to use the first UWB transceiver to transmit updated software to the second UWB transceiver.

The controller, in some aspects, is further adapted to determine a type of patient support apparatus the second UWB transceiver is incorporated into and forward the type of patient support apparatus to the transceiver for display on the computer.

The type of patient support apparatus, in some aspects, includes at least one of the following: a bed or a stretcher.

The controller, in some aspects, is further adapted to perform the following: (i) use the first UWB transceiver to obtain a second identifier from a third UWB transceiver onboard the patient support apparatus; (ii) determine a second location of the third UWB transceiver onboard the patient support apparatus based on the second identifier; and (iii) forward the second identifier and the second location of the third UWB transceiver to the transceiver for display on the computer.

In some aspects, the transceiver is coupled to a Universal Serial Bus adapted to couple to the computer.

In some aspects, the transceiver is a wireless transceiver adapted to communicate with the computer.

The controller, in some aspects, is further adapted to perform the following: (i) use the first UWB transceiver to obtain a second identifier from a third UWB transceiver; (ii) use the second identifier to determine whether the third UWB transceiver is positioned onboard the patient support apparatus or positioned onboard a second device; and (iii) forward location data to the transceiver for display on the computer. The location data indicates whether the third UWB transceiver is positioned onboard the patient support apparatus or positioned onboard the second device.

The controller, in some aspects, is further adapted to identify the second device and to forward the identity of the second device to the transceiver for display on the computer.

In some aspects, the controller is further adapted to listen to all UWB traffic detected by the first UWB transceiver and to record the UWB traffic in a file.

The controller, in some aspects, is further adapted to forward an indication to the transceiver when the tool is positioned in a location where the first UWB transceiver is not able to detect any UWB signals from the second UWB transceiver or any other UWB transceiver.

In some aspects, the controller is further adapted to forward a test command to the patient support apparatus instructing the patient support apparatus to perform an action.

The controller, in some aspects, is further adapted to forward a dummy signal to the locator unit wherein the dummy signal imitates a signal the patient support apparatus is configured to send to the locator unit.

The controller, in some aspects, is further adapted to retrieve from the second UWB transceiver a set of devices the second UWB transceiver has previously ranged with.

In some aspects, the set of devices includes at least the last twenty devices the second UWB transceiver has ranged with prior to ranging with the first UWB transceiver.

In some aspects, the tool further includes a first Bluetooth transceiver adapted to communicate with a second Bluetooth transceiver onboard the patient support apparatus.

The controller, in some aspects, is further adapted to send a command to the patient support apparatus to perform at least one of the following: illuminate a light on the patient support apparatus, display an indicator on a display of the patient support apparatus, or emit a sound from the patient support apparatus.

According to another aspect of the present disclosure, a software application embodied in a non-transitory computer readable medium is provided. The software application is adapted, when executed by a controller of a computing device, to cause the computing device to perform the following: (a) use a first UWB transceiver to obtain an identifier from a second UWB transceiver onboard a patient support apparatus; (b) determine a location of the second UWB transceiver onboard the patient support apparatus based on the identifier; and (c) display on a display the location of the second UWB transceiver.

According to still another aspect of the present disclosure, a software application embodied in a non-transitory computer readable medium is provided. The software application is adapted, when executed by a controller of a computing device, to cause the computing device to perform the following: (a) use a first UWB transceiver to obtain an identifier from a second UWB transceiver; (b) determine whether the second UWB transceiver is onboard a patient support apparatus or onboard a locator unit based on the identifier; and (c) display on a display data indicating whether the second UWB transceiver is onboard the patient support apparatus or onboard the locator unit.

According to other aspects of the present disclosure, the software application is adapted to instruct the controller to determine a distance between the first UWB transceiver and the second UWB transceiver by using the first UWB transceiver to range with the second UWB transceiver using ultra-wideband.

In some aspects, the software application is adapted to instruct the controller to display the distance on the display.

The software application, in some aspects, is adapted to instruct the controller to measure a quality of UWB signals sent by the second UWB transceiver and detected by the first UWB transceiver, as well as to instruct the controller to display the measurement of quality on the display.

In some aspects, the software application is adapted to instruct the controller to use the first UWB transceiver to retrieve error codes from the second UWB transceiver, and to instruct the controller to display the error codes on the display.

In some aspects, the software application is adapted to instruct the controller to use the first UWB transceiver to transmit updated software to the second UWB transceiver.

The software application, in some aspects, is adapted to instruct the controller to determine a type of patient support apparatus the second UWB transceiver is incorporated into and to display the type of patient support apparatus on the display.

The type of patient support apparatus, in some aspects, includes at least one of the following: a bed or a stretcher.

In some aspects, the software application is adapted to instruct the controller to perform the following: (i) use the first UWB transceiver to obtain a second identifier from a third UWB transceiver onboard the patient support apparatus; (ii) determine a second location of the third UWB transceiver onboard the patient support apparatus based on the second identifier; and (iii) display the second identifier and the second location of the third UWB transceiver on the display.

In some aspects, the software application is adapted to instruct the controller to perform the following: (i) use the first UWB transceiver to obtain a second identifier from a third UWB transceiver; (ii) use the second identifier to determine whether the third UWB transceiver is positioned onboard the patient support apparatus or positioned onboard a second device; and (iii) display location data on the display, wherein the location data indicates whether the third UWB transceiver is positioned onboard the patient support apparatus or positioned onboard the second device.

In some aspects, the software application is adapted to instruct the controller to identify the second device and to display the identity of the second device on the display.

The software application, in some aspects, is adapted to instruct the controller to listen to all UWB traffic detected by the first UWB transceiver and to record the UWB traffic in a file.

The software application, in some aspects, is adapted to instruct the controller to display an indicator on the display when the first UWB transceiver is not able to detect any UWB signals from the second UWB transceiver or any other UWB transceiver.

In some aspects, the software application is adapted to instruct the controller to forward a test command to the patient support apparatus instructing the patient support apparatus to perform an action.

The software application, in some aspects, is adapted to instruct the controller forward a dummy signal to the locator unit wherein the dummy signal imitates a signal the patient support apparatus is configured to send to the locator unit.

In some aspects, the software application is adapted to instruct the controller to retrieve from the second UWB transceiver a set of devices the second UWB transceiver has previously ranged with.

The set of devices, in some aspects, includes at least the last twenty devices the second UWB transceiver has ranged with prior to ranging with the first UWB transceiver.

The software application, in some aspects, is adapted to instruct the controller to communicate with a Bluetooth transceiver onboard the patient support apparatus.

The software application, in some aspects, is adapted to instruct the controller to send a command to the patient support apparatus to perform at least one of the following: illuminate a light on the patient support apparatus, display an indicator on a display of the patient support apparatus, or emit a sound from the patient support apparatus.

In some aspects, the software application is adapted to be executed on a smart phone into which is integrated the first UWB transceiver and the display.

In some aspects, the software application is adapted to be executed on a personal computer into which is integrated the display.

In some aspects, the first UWB transceiver is contained in a stand-alone housing and the software application is adapted to communicate with the first UWB transceiver via a cable coupled between the stand-alone housing and the personal computer.

In some aspects, the first UWB transceiver is contained in a stand-alone housing and the software application is adapted to communicate with the first UWB transceiver via a wireless connection between the stand-alone housing and the personal computer.

In some aspects, the first UWB transceiver is integrated into the personal computer and the software application is adapted to communicate with the first UWB transceiver via internal conductors.

According to another aspect of the present disclosure, a portable tool is provided for communicating a software update to a device. The portable tool includes a housing, a first ultra-wideband (UWB) transceiver, and a software update control. The first UWB transceiver is adapted to communicate with a second UWB transceiver positioned on the device. The software update control is adapted to send updated software to the device when activated by a user. The controller is adapted to perform the following: (a) transmit a first query from the first UWB transceiver to the second UWB transceiver requesting a software identifier indicating a current version of software on the device; (b) determine a distance between the first UWB transceiver and the second UWB transceiver; (c) enable the software update control if the distance between the first UWB transceiver and the second UWB transceiver is less than a threshold; and (d) disable the software update control if the distance between the first UWB transceiver and the second UWB transceiver is more than the threshold.

According to other aspects of the present disclosure, the portable tool may further comprise a software installation control that when activated by a user, is adapted to command the device to install the updated software. The controller may further be adapted to perform the following: (e) transmit a second query to the device requesting an indication of whether the device is in a first state in which the device is able to install the updated software or a second state in which the device is not able to install the updated software; (f) enable the software installation control if the device is in the first state; and (g) disable the software installation control if the device is in the second state.

According to some aspects, the device is a patient support apparatus.

In some aspects, the device is a locator unit adapted to provide a wireless signal indicative of a location of the locator unit.

The first state, in some aspects, corresponds to no patient being detected on the patient support apparatus and the second state corresponds to a patient being detected on the patient support apparatus.

The first state, in some aspects, corresponds to an exit detection system being disarmed and the second state corresponds to the exit detection system being armed. The exit detection system is adapted to issue an alert, when armed, in response to a patient exiting the patient support apparatus.

The first state, in some aspects, corresponds to a monitoring system being disarmed and the second state corresponds to the monitoring system being armed. The monitoring system is adapted to monitor a plurality of different components of the patient support apparatus.

The controller, in some aspects, is adapted to display the distance between the first UWB transceiver and the second UWB transceiver.

The portable tool, in some aspects, further includes a third UWB transceiver adapted to determine a second distance between the third UWB transceiver and the second UWB transceiver.

The controller, in some aspects, is adapted to transmit a security certificate to the device when sending the updated software to the device.

In some aspects, the controller is further adapted to send a command to the device instructing the device to use the second UWB transceiver to determine a measured second distance between the second UWB transceiver and a third UWB transceiver positioned onboard the device, wherein the third UWB transceiver is positioned at a known second distance away from the second UWB transceiver.

The controller, in some aspects, is adapted to determine a difference between the measured second distance and the known second distance and issue a notification if the difference exceeds a second threshold.

In some aspects, the controller is further adapted to send a command to the device instructing the device to use the second UWB transceiver to determine a measured second distance between a third UWB transceiver and a fourth UWB transceiver, wherein the third UWB transceiver is positioned at a known second distance away from the fourth UWB transceiver.

The controller, in some aspects, is adapted to determine a difference between the measured second distance and the known second distance and issue a notification if the difference exceeds a second threshold.

The third and fourth UWB transceivers, in some aspects, are positioned on a second device spaced from the device.

According to another aspect of the present disclosure, a software application embodied in a non-transitory computer readable medium is provided. The software application is adapted, when executed by a controller of a computing device, to cause the computing device to perform the following: wirelessly send updated software to a device when a software update control is activated by a user; transmit a first query from a first UWB transceiver of the computing device to a second UWB transceiver onboard the device, wherein the first query requests a software identifier indicating a current version of software on the device; determine a distance between the first UWB transceiver and the second UWB transceiver; enable the software update control if the distance between the first UWB transceiver and the second UWB transceiver is less than a threshold; and disable the software update control if the distance between the first UWB transceiver and the second UWB transceiver is more than the threshold.

The software application, in some aspects, is adapted to cause the computing device to perform the following: transmit a command to the device to install the updated software in response to a software installation control being activated by the user; transmit a second query to the device requesting an indicating of whether the device is in a first state in which the device is able to install the updated software or a second state in which the device is not able to install the updated software; enable the software installation control if the device is in the first state; and disable the software installation control if the device is in the second state.

In some aspects, the device is a patient support apparatus.

In some aspects, the device is a locator unit adapted to provide a wireless signal indicative of a location of the locator unit.

The first state, in some aspects, includes no patient being detected on the patient support apparatus and the second state includes a patient being detected on the patient support apparatus.

The first state, in some aspects, includes an exit detection system being disarmed and the second state includes the exit detection system being armed, wherein the exit detection system is adapted to issue an alert, when armed, in response to a patient exiting the patient support apparatus.

The first state, in some aspects, includes a monitoring system being disarmed and the second state includes the monitoring system being armed, wherein the monitoring system is adapted to monitor a plurality of different components of the patient support apparatus.

The software application, in some aspects, is adapted to cause the computing device to display the distance between the first UWB transceiver and the second UWB transceiver.

In some aspects, the software application is adapted to cause the computing device to use a third UWB transceiver to determine a second distance between the third UWB transceiver and the second UWB transceiver.

In some aspects, the software application is adapted to cause the computing device to transmit a security certificate to the device when sending the updated software to the device.

In some aspects, the software application is adapted to cause the computing device to send a command to the device instructing the device to use the second UWB transceiver to measure a second distance between the second UWB transceiver and a third UWB transceiver positioned onboard the device, wherein the third UWB transceiver is positioned at a known second distance away from the second UWB transceiver.

The software application, in some aspects, is adapted to cause the computing device to determine a difference between the measured second distance and the known second distance and issue a notification if the difference exceeds a second threshold.

The software application, in some aspects, is adapted to cause the computing device to send a command to the device instructing the device to use the second UWB transceiver to measure a second distance between a third UWB transceiver and a fourth UWB transceiver, wherein the third UWB transceiver is positioned at a known second distance away from the second UWB transceiver.

In some aspects, the software application is adapted to cause the computing device to determine a difference between the measured second distance and the known second distance and issue a notification if the difference exceeds a second threshold.

The third and fourth UWB transceivers, in some aspects, are positioned on a second device spaced from the device.

According to another aspect of the present disclosure, a portable tool is provided for communicating with a device. The tool includes a housing, a first UWB transceiver, a distance-verification control, and a controller. The first UWB transceiver is adapted to communicate with a second UWB transceiver positioned on the device. The distance-verification control is adapted to send a command to the device instructing the device to use the second UWB transceiver to determine a first measured distance between the second UWB transceiver and a third UWB transceiver. The third UWB transceiver is positioned at a first known distance away from the second UWB transceiver. The controller is adapted to issue a notification if the first measured distance differs from the first known distance by more than a threshold.

According to other aspects, the portable tool further includes a software update control adapted to send updated software to the device when activated by a user. The controller, in some aspects, is further adapted to (a) transmit a first query from the first UWB transceiver to the second UWB transceiver requesting a software identifier indicating a current version of software on the device; (b) determine a second distance between the first UWB transceiver and the second UWB transceiver; (c) enable the software update control if the second distance between the first UWB transceiver and the second UWB transceiver is less than a second threshold; and (d) disable the software update control if the second distance between the first UWB transceiver and the second UWB transceiver is more than the second threshold.

In some aspects, the portable tool further includes a software installation control that, when activated by a user, is adapted to command the device to install the updated software. The controller is further adapted, in some aspects, to (e) transmit a second query to the device requesting an indicating of whether the device is in a first state in which the device is able to install the updated software or a second state in which the device is not able to install the updated software; (f) enable the software installation control if the device is in the first state; and (g) disable the software installation control if the device is in the second state.

In some aspects, the device is a patient support apparatus or a locator unit adapted to provide a wireless signal indicative of a location of the locator unit.

The first state, in some aspects, corresponds to no patient being detected on the patient support apparatus and the second state corresponds to a patient being detected on the patient support apparatus.

The first state, in some aspects, corresponds to an exit detection system being disarmed and the second state corresponds to the exit detection system being armed.

The first state, in some aspects, corresponds to a monitoring system being disarmed and the second state corresponds to the monitoring system being armed.

The controller, in some aspects, is adapted to display the second distance between the first UWB transceiver and the second UWB transceiver.

The controller, in some aspects, is adapted to transmit a security certificate to the device when sending the command to the device.

The third UWB transceiver, in some aspects, is positioned onboard the device.

The controller, in some aspects, is further adapted to send a second command to the device instructing the device to use the second UWB transceiver to determine a measured second distance between the third UWB transceiver and a fourth UWB transceiver, wherein the third UWB transceiver is positioned at a known second distance away from the fourth UWB transceiver.

In some aspects, the controller is adapted to issue a second notification if a difference between the measured second distance and the known second difference exceeds a second threshold.

In some aspects, the third and fourth UWB transceivers are positioned on a second device spaced from the device.

The controller, in some aspects, is adapted to determine a position of the device relative to the portable tool and to display the position of the device on a display of the portable tool.

According to another aspect of the present disclosure, a software application embodied in a non-transitory computer readable medium is provided. The software application is adapted, when executed by a controller of a computing device, to cause the computing device to perform the following: wirelessly send a command from a first UWB transceiver of the computing device to a device instructing the device to use a second UWB transceiver to determine a first measured distance between the second UWB transceiver and a third UWB transceiver, wherein the third UWB transceiver is positioned at a first known distance away from the second UWB transceiver; and issue a notification if the first measured distance differs from the first known distance by more than a threshold.

According to other aspects of the present disclosure, the software application may be further adapted to cause the computing device to send updated software to the device when activated by a user; to transmit a first query from the first UWB transceiver to the second UWB transceiver requesting a software identifier indicating a current version of software on the device; to determine a second distance between the first UWB transceiver and the second UWB transceiver; to enable the software update control if the second distance between the first UWB transceiver and the second UWB transceiver is less than a second threshold; and to disable the software update control if the second distance between the first UWB transceiver and the second UWB transceiver is more than the second threshold.

In some aspects, the software application is adapted to cause the computing device to transmit a command to the device to install the updated software in response to a software installation control being activated by the user; to transmit a second query to the device requesting an indicating of whether the device is in a first state in which the device is able to install the updated software or a second state in which the device is not able to install the updated software; to enable the software installation control if the device is in the first state; and to disable the software installation control if the device is in the second state.

In some aspects, the device is a patient support apparatus or a locator unit adapted to provide a wireless signal indicative of a location of the locator unit.

The first state, in some aspects, corresponds to no patient being detected on the patient support apparatus and the second state corresponds to a patient being detected on the patient support apparatus.

The first state, in some aspects, corresponds to an exit detection system being disarmed and the second state corresponds to the exit detection system being armed.

The first state, in some aspects, corresponds to a monitoring system being disarmed and the second state corresponds to the monitoring system being armed.

The controller, in some aspects, is adapted to display the second distance between the first UWB transceiver and the second UWB transceiver.

The software application, in some aspects, is adapted to cause the computing device to use a third UWB transceiver to determine a third distance between the third UWB transceiver and the second UWB transceiver.

In some aspects, the software application is adapted to cause the computing device to transmit a security certificate to the device when sending the command to the device.

The software application, in some aspects, is adapted to cause the computing device to send a second command to the device instructing the device to use the second UWB transceiver to measure a second distance between a third UWB transceiver and a fourth UWB transceiver, wherein the third UWB transceiver is positioned at a known second distance away from the second UWB transceiver.

In some aspects, the software application is adapted to cause the computing device to issue a second notification if a difference between the known second distance and the measured second distance exceeds a second threshold.

In some aspects, the third and fourth UWB transceivers are positioned on a second device spaced from the device.

The software application, in some aspects, is adapted to cause the computing device to determine a position of the device relative to a portable tool and to display the position of the device on a display.

According to yet another aspect of the present disclosure, a patient support apparatus is provided that includes a support surface adapted to support a patient, a first UWB transceiver, and a controller. The first UWB transceiver is adapted to wirelessly communicate with a second UWB transceiver onboard a portable tool. The controller is adapted to determine a distance between the first UWB transceiver and the second UWB transceiver, to accept a software update from the portable tool if the distance between the first UWB transceiver and the second UWB transceiver is less than a threshold, and to reject the software update if the distance between the first UWB transceiver and the second UWB transceiver is more than the threshold.

In other aspects of the present disclosure, the controller is further adapted to determine whether the patient support apparatus is in a first state or a second state; to allow installation of the software update if the patient support apparatus is in the first state; and to disallow installation of the software update if the patient support apparatus is in the second state.

The first state, in some aspects, corresponds to no patient being detected on the patient support apparatus and the second state corresponds to a patient being detected on the patient support apparatus.

The first state, in some aspects, corresponds to an exit detection system of the patient support apparatus being disarmed and the second state corresponds to the exit detection system being armed.

The first state, in some aspects, corresponds to a monitoring system of the patient support apparatus being disarmed and the second state corresponds to the monitoring system being armed.

The controller, in some aspects, is adapted to display the distance between the first UWB transceiver and the second UWB transceiver.

The third UWB transceiver, in some aspects, is adapted to determine a second distance between the third UWB transceiver and the second UWB transceiver.

The controller, in some aspects, is adapted to analyze a security certificate from the portable tool prior to installing the software update.

The controller, in some aspects, is adapted to determine a measured second distance between the first UWB transceiver and a third UWB transceiver positioned onboard the patient support apparatus, wherein the first UWB transceiver is positioned at a known second distance away from the third UWB transceiver.

The controller, in some aspects, is adapted to determine a difference between the measured second distance and the known second distance and issue a notification if the difference exceeds a second threshold.

The controller, in some aspects, is adapted to determine a measured second distance between a third UWB transceiver and a fourth UWB transceiver, wherein the third UWB transceiver is positioned at a known second distance away from the fourth UWB transceiver.

In some aspects, the controller is adapted to determine a difference between the measured second distance and the known second distance and issue a notification if the difference exceeds a second threshold.

The third and fourth UWB transceivers, in some aspects, are positioned on a device spaced from the patient support apparatus.

The third and fourth UWB transceivers, in some aspects, are positioned onboard the patient support apparatus.

According to yet another aspect of the present disclosure, a patient support apparatus is provided that includes a support surface adapted to support a patient, a first UWB transceiver, a second UWB transceiver, and a controller. The controller is adapted to, in response to a trigger, determine a first measured distance between the first UWB transceiver and the second UWB transceiver. The first UWB transceiver is positioned at a first known distance away from the second UWB transceiver. The controller is further adapted to issue a notification if the first measured distance differs from the first known distance by more than a threshold.

According to other aspects of the present disclosure, the controller is adapted to determine a second distance between the first UWB transceiver and a third UWB transceiver onboard a portable tool, to accept a software update from the portable tool if the second distance between the first UWB transceiver and the third UWB transceiver is less than a second threshold, and to reject the software update if the second distance between the first UWB transceiver and the third UWB transceiver is more than the second threshold.

The controller, in some aspects, is further adapted to determine whether the patient support apparatus is in a first state or a second state; to allow installation of the software update if the patient support apparatus is in the first state; and to disallow installation of the software update if the patient support apparatus is in the second state.

In some aspects, the first state corresponds to no patient being detected on the patient support apparatus and the second state corresponds to a patient being detected on the patient support apparatus.

The first state, in some aspects, corresponds to an exit detection system of the patient support apparatus being disarmed and the second state corresponds to the exit detection system being armed.

The first state, in some aspects, corresponds to a monitoring system of the patient support apparatus being disarmed and the second state corresponds to the monitoring system being armed.

In some aspects, the controller is further adapted to display the first measured distance between the first UWB transceiver and the second UWB transceiver.

The patient support apparatus, in some aspects, includes a third UWB transceiver adapted to determine a second distance between the third UWB transceiver and the second UWB transceiver.

The controller, in some aspects, is adapted to analyze a security certificate from the portable tool prior to installing the software update.

The controller, in some aspects, is adapted to determine a measured second distance between the first UWB transceiver and a third UWB transceiver positioned onboard the patient support apparatus, wherein the first UWB transceiver is positioned at a known second distance away from the third UWB transceiver.

In some aspects, the controller is adapted to determine a difference between the measured second distance and the known second distance and issue a second notification if the difference exceeds a second threshold.

The controller, in some aspects, is further adapted to determine a measured second distance between a third UWB transceiver and a fourth UWB transceiver, wherein the third UWB transceiver is positioned at a known second distance away from the fourth UWB transceiver.

In some aspects, the controller is adapted to determine a difference between the measured second distance and the known second distance and issue a second notification if the difference exceeds a second threshold.

The third and fourth UWB transceivers, in some aspects, are positioned on a device spaced from the patient support apparatus.

The third and fourth UWB transceivers, in some aspects, are positioned onboard the patient support apparatus.

The trigger, in some aspects, includes one or more of (a) a receipt of a command from a portable tool; (b) an activation of a control onboard the patient support apparatus; or (c) a passage of an amount of time.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 6 is an example of a data screen displayable on the first or second portable communication tools;

FIG. 9 is a block diagram of a patient support apparatus, the portable communication tool, and a locator unit, illustrating several distance measurements that may be taken in response to a trigger.

DETAILED DESCRIPTION OF THE EMBODIMENTS

Figure 1:
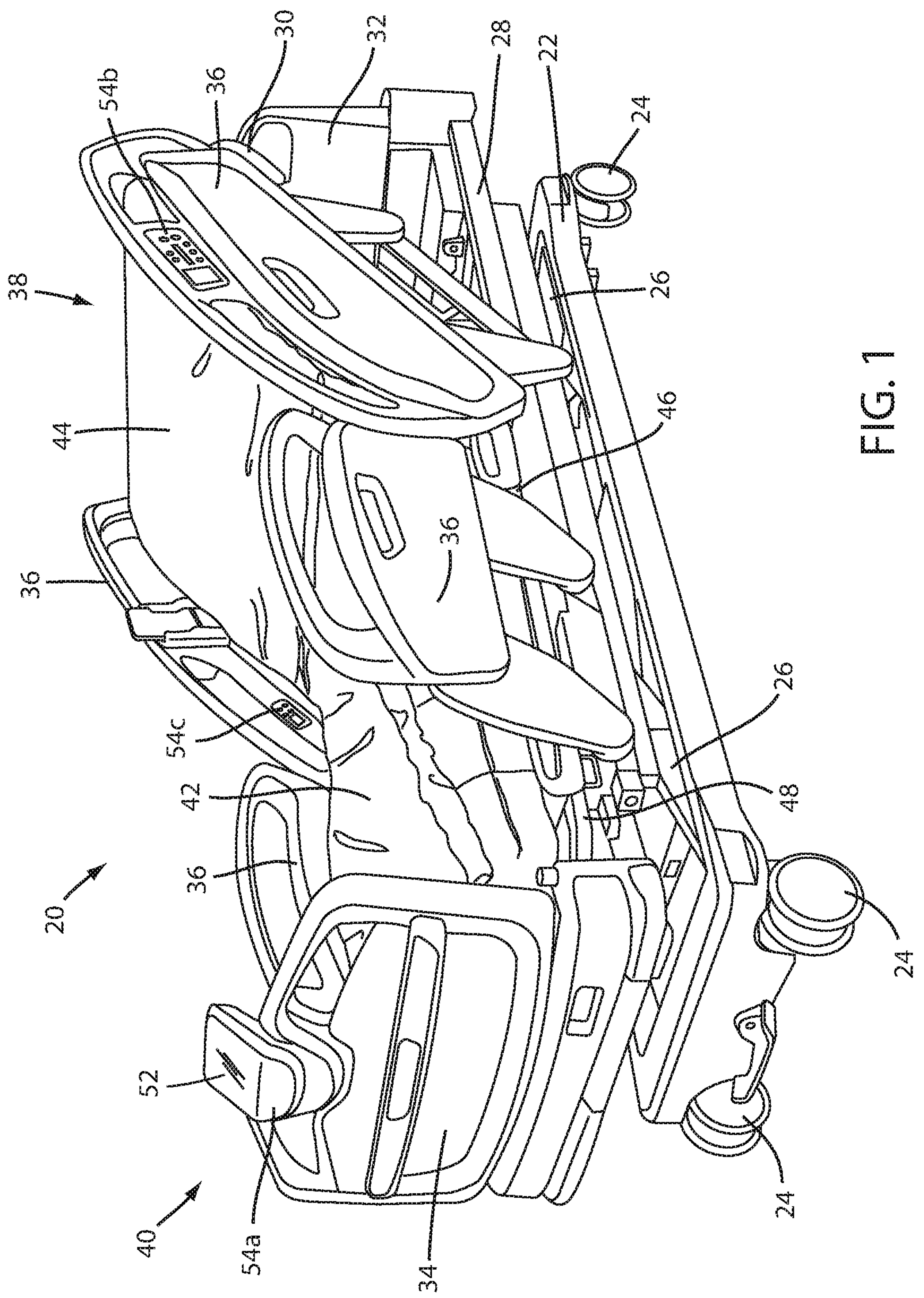
FIG. 1 is a perspective view of a patient support apparatus according to a first embodiment of the present disclosure.

An illustrative patient support apparatus 20 according to an embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, an operating table, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. In some embodiments, the mattress 42 includes one or more inflatable bladders that are controllable via a blower, or other source of pressurized air. In at least one embodiment, the inflation of the bladders of the mattress 42 is controllable via electronics built into patient support apparatus 20. In one such embodiments, mattress 42 may take on any of the functions and/or structures of any of the mattresses disclosed in commonly assigned U.S. Pat. No. 9,468,307 issued Oct. 18, 2016, to inventors Patrick Lafleche et al., the complete disclosure of which is incorporated herein by reference. Still other types of mattresses may be used.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width and/or length of patient support deck 30, thereby allowing patient support apparatus 20 to accommodate patients of varying sizes. When so modified, the width of deck 30 may be adjusted sideways and/or lengthwise in increments or otherwise.

As used herein, the term “longitudinal” refers to a direction parallel to an axis between the head end 38 and the foot end 40. The terms “transverse” or “lateral” refer to a direction perpendicular to the longitudinal direction and parallel to a surface on which the patient support apparatus 20 rests.

It will be understood by those skilled in the art that patient support apparatus 20 can be designed with other types of mechanical constructions that are different from what is shown in the attached drawings, such as, but not limited to, the construction described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may include the same, or nearly the same, structures as the Model 3002 S3 bed manufactured and sold by Stryker Corporation of Kalamazoo, Michigan. This construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. In still another embodiment, the mechanical construction of patient support apparatus 20 may include the same, or nearly the same, structure as the Model 3009 Procuity MedSurg bed manufactured and sold by Stryker Corporation of Kalamazoo, Michigan. This construction is described in greater detail in the Stryker Maintenance Manual for the 3009 Procuity MedSurg bed (publication 3009-009-002, Rev. A.0), published in 2020 by Stryker Corporation of Kalamazoo, Michigan.

It will be understood by those skilled in the art that patient support apparatus 20 can be designed with still other types of mechanical constructions, such as, but not limited to, those described in commonly assigned, U.S. Pat. No. 769, 059 issued Apr. 6, 2010, to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The overall mechanical construction of patient support apparatus 20 may also take on still other forms different from what is disclosed in the aforementioned references provided the patient support apparatus includes one or more of the functions, features, and/or structures discussed in greater detail below.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel 54*a*, a pair of outer siderail control panels 54*b* (only one of which is visible), and a pair of inner siderail control panels 54*c* (only one of which is visible). Footboard control panel 54*a* and outer siderail control panels 54*b* are intended to be used by caregivers, or other authorized personnel, while inner siderail control panels 54*c* are intended to be used by the patient associated with patient support apparatus 20. Each of the control panels 54 includes a plurality of controls, although each control panel 54 does not necessarily include the same controls and/or functionality.

Among other functions, the controls of control panel 54*a* allow a user to control one or more of the following: change a height of support deck 30; raise or lower head section 44; activate and deactivate a brake for wheels 24; arm and disarm an exit detection system 136 and/or an onboard monitoring system 138 (FIG. 3); change various settings on patient support apparatus 20; view the current location of the patient support apparatus 20 as determined by the location detection system discussed herein; view what ultra-wideband (UWB) devices, such as, but not limited to, medical devices, exercise devices, nurse call devices, caregiver badges, locator units, etc. that the patient support apparatus 20 has associated itself with; and perform other actions. One or both of the inner siderail control panels 54*c* also include at least one control that enables a patient to call a remotely located nurse (or other caregiver). In addition to the nurse call control, one or both of the inner siderail control panels 54*c* also include one or more controls for controlling one or more features of one or more room devices positioned within the same room as the patient support apparatus 20. Such room devices include, but are not necessarily limited to, a television, a reading light, and a room light. With respect to the television, the features that may be controllable by one or more controls on control panel 54*c* include, but are not limited to, the volume, the channel, the closed-captioning, and/or the power state of the television. With respect to the room and/or night lights, the features that may be controlled by one or more controls on control panel 54*c* include the on/off state and/or the brightness level of these lights.

Figure 3:
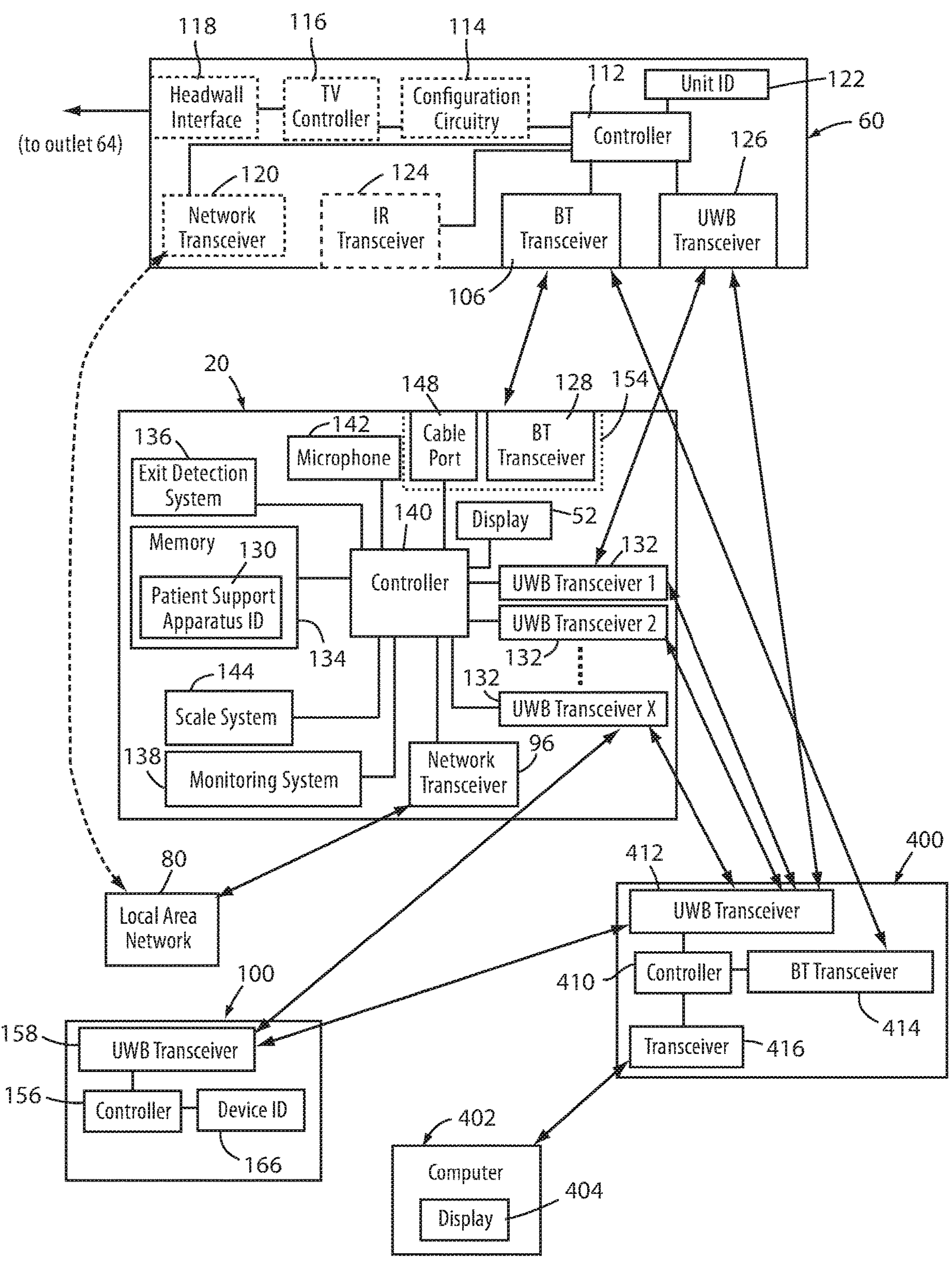
FIG. 3 is a block diagram of the patient support apparatus, locator unit, and first communication tool of FIG. 2.

Control panel 54*a* includes a display 52 (FIG. 1) configured to display a plurality of different screens thereon. Such screens may include an exit detection control screen that includes one or more icons that, when touched, control an onboard exit detection system 136 (FIG. 3). The exit detection system 136 is as adapted to issue an alert when a patient exits from patient support apparatus 20. Exit detection system 136 may include any of the same features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. Other types of exit detection systems may be included within patient support apparatus 20.

Control panel 54*a* may also include a monitoring control screen that includes a plurality of control icons that, when touched, control and onboard monitoring system 138 (FIG. 3) built into patient support apparatus 20. The onboard monitoring system 138 alerts the caregiver through a unified indicator, such as a light or a plurality of lights controlled in a unified manner, when any one or more of a plurality of settings on patient support apparatus 20 are in an undesired state, and uses that same unified indicator to indicate when all of the plurality of settings are in their respective desired states. Stated alternatively, monitoring system 138, when armed, monitors a plurality of conditions of patient support apparatus 20 (such as, but not limited to, any one or more of the following: brake status, siderail position, litter frame height, exit detection system 136, A/C cord status, nurse call cable status, etc.) and issues an alert if any one of those conditions are in an undesired state. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of monitoring systems may be included within patient support apparatus 20.

Control panel 54*a* may also include a scale control screen that includes a plurality of control icons that, when touched, control a scale system 144 (FIG. 3) of patient support apparatus 20. Such a scale system 144 may include any of the same features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference. The scale system may utilize the same force sensors and/or other components that are utilized by the exit detection system 136, or it may utilize one or more different sensors and/or other components. Other scale systems besides those mentioned above in the '254 and '954 applications may alternatively be included within patient support apparatus 20.

Control panel 54 may also include a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of motion control screens may be included on patient support apparatus 20.

Control panel 54*a* may also include a motion lock control screen that includes a plurality of control icons that, when touched, control one or more motion lockout functions of patient support apparatus 20. Such motion lockout functions typically include the ability for a caregiver to use control panel 54*a* to lock out one or more of the motion controls of the patient control panels 54*c* such that the patient is not able to use the motion controls on control panels 54*c* (and/or 54b) to control the movement of one or more components of patient support apparatus 20. The motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosure of which is incorporated herein by reference. Other types of motion lockouts may be included within patient support apparatus 20.

Control panel 54*a* may also include a menu screen that includes a plurality of menu icons that, when touched, bring up one or more additional screens for controlling and/or viewing one or more other aspects of patient support apparatus 20. Such other aspects include, but are not limited to, displaying information about one or more UWB devices that are currently associated with patient support apparatus 20, diagnostic and/or service information for patient support apparatus 20, mattress control and/or status information, configuration settings, location information, and other settings and/or information. As will be discussed in greater detail below, patient support apparatus 20 includes an onboard locating system that is adapted to automatically determine the relative position of one or more UWB devices with respect to patient support apparatus 20 and, in some instances, automatically associate and/or disassociate those UWB devices with and/or from patient support apparatus 20 (and/or the patient assigned to patient support apparatus 20) depending upon the proximity of the UWB device to patient support apparatus 20. Further details of this locating system are provided below.

Figure 2:
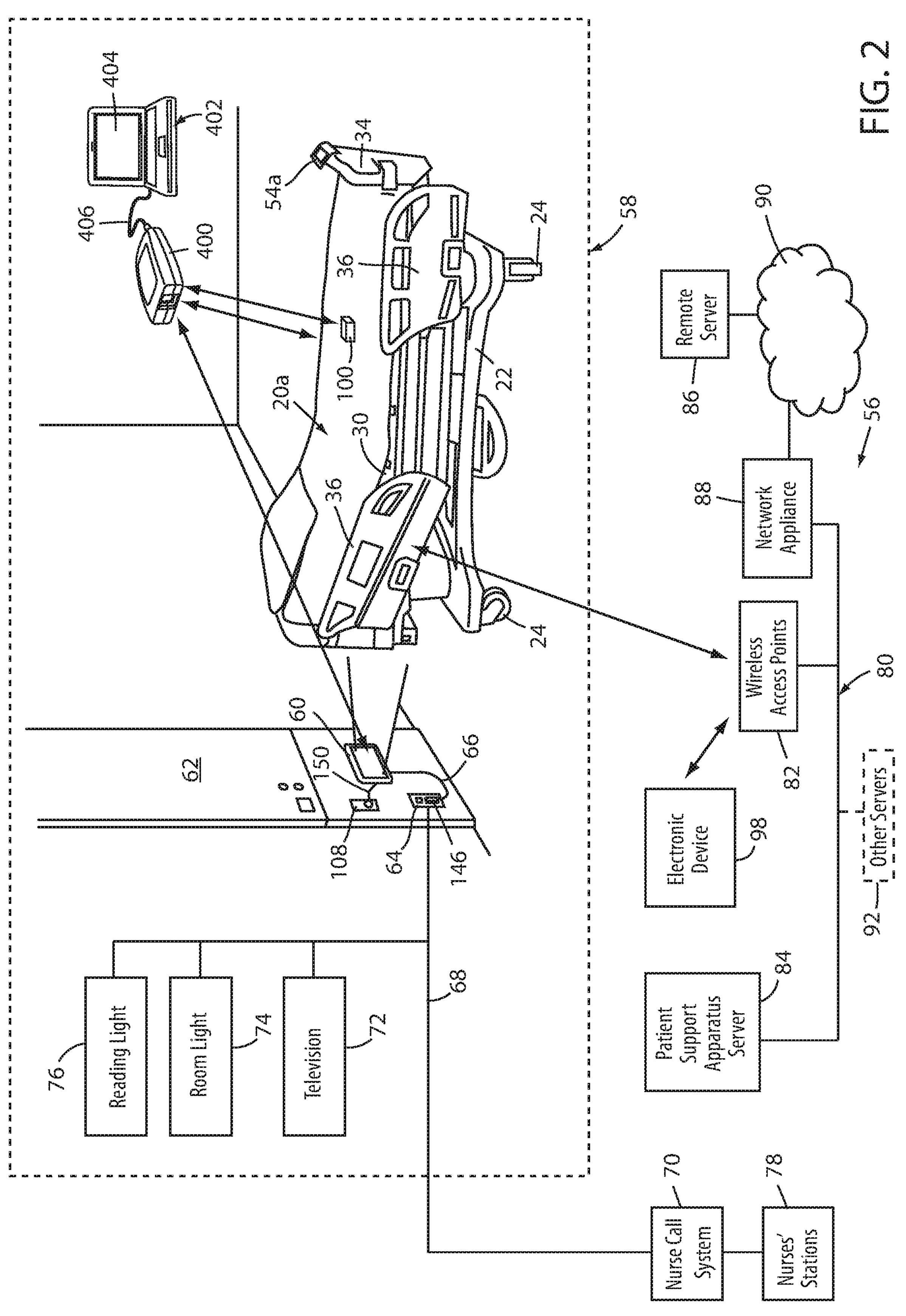
FIG. 2 is a diagram of the patient support apparatus of FIG. 1, a locator unit, a first portable communication tool, and as an example of the IT infrastructure of a typical healthcare facility.

FIG. 2 illustrates patient support apparatus 20 positioned within a room 58 of a healthcare facility. FIG. 2 also illustrates additional items that may be present in a healthcare facility and which patient support apparatus 20 is configured to communicate with, including, but not limited to, a locator unit 60, a conventional local area network 80 of the healthcare facility, and one or more devices 100 used during the care of a patient. Still further, FIG. 2 illustrates a portable communication tool 400 that a technician may use to communicate with, and troubleshoot, patient support apparatus 20, locator unit 60, and/or other devices 100 positioned within room 58. Locator units 60 are positioned at known and fixed locations within the healthcare facility in which patient support apparatus 20 is positioned. Locator units 60 function as fixed locators. That is, locator units 60 communicate with patient support apparatuses 20 and share information with them that allows the location of the patient support apparatuses 20 to be determined, as well as the location of any devices 100 that are associated with patient support apparatus 20.

In some embodiments, patient support apparatus 20 is configured to be able to communicate with at least two different types of locator units 60: linked locator units and unlinked locator units. One example of a linked locator unit 60 is shown in FIG. 2. Examples of unlinked locator units 60 are shown (and referred to as unlinked locator units 60*b*) in commonly assigned U.S. patent application Ser. No. 63/306,279 filed Feb. 3, 2022, by inventors Madhu Sandeep Thota et al. and entitled COMMUNICATION SYSTEM FOR PATIENT SUPPORT APPARATUSES, the complete disclosure of which is incorporated herein by reference. Other examples of unlinked locator units 60 are shown (and referred to as unlinked locator units 60*a*) in commonly assigned U.S. patent application Ser. No. 63/356,061 filed Jun. 28, 2022, by inventors Krishna Bhimavarapu et al. and entitled BADGE AND PATIENT SUPPORT APPARATUS COMMUNICATION SYSTEM, the complete disclosure of which is incorporated herein by reference. Patient support apparatus 20 is configured to communicate with the unlinked locator units described in either of the aforementioned '279 or '061 applications and/or to perform any one or more of the functions described therein that utilize such unlinked locator units and/or information provided by such unlinked locator units. Unless explicitly stated otherwise, all references herein to "locator units 60" without the term "linked" or "unlinked" in the reference will refer to both linked and unlinked locator units 60.

Linked locator units 60 are adapted to be communicatively linked to a conventional communication outlet 64 and are adapted to provide location information to patient support apparatus 20. Linked locator units 60 are also adapted to serve as a communication conduit for routing wireless communications between patient support apparatus 20 and one or more devices and/or systems that are communicatively coupled to communication outlet 64 (e.g. room devices 72, 74, 76, and/or nurse call system 70, FIG. 2). In general, linked locator units 60 are typically positioned in patient rooms of the healthcare facility where one or more communication outlets 64 are typically present.

As shown in FIG. 2, linked locator unit 60 is adapted to be mounted to a wall 62, such as a headwall of a patient room 58 within the healthcare facility. The headwall of a conventional healthcare facility room 58 typically includes a conventional communications outlet 64 physically integrated therein. Communications outlet 64 is adapted to receive a nurse call cable 66 that physically connects at its other end either to patient support apparatus 20 (not shown) or to linked locator unit 60 (shown in FIG. 2). In many healthcare facilities, communication outlet 64 includes a 37-pin connector, although other types of connectors are often found in certain healthcare facilities. As will be discussed in greater detail below, linked locator unit 60 and nurse call cable 66 allow patient support apparatus 20 to communicate with a nurse call system 70, and one or more room devices positioned within room 58.

Communication outlet 64 is electrically coupled to one or more cables, wires, or other type of conductors 68 that electrically couple the communication outlet 64 to a nurse call system 70 and one or more conventional room devices, such as a television 72, a room light 74, and/or a reading light 76. Conductors 68 are typically located behind wall 62 and not visible. In some healthcare facilities, conductors 68 may first couple to a room interface circuit board that includes one or more conductors 68 for electrically coupling the room interface circuit board to room device 72, 74, 76 and/or nurse call system 70. Still other communicative arrangements for coupling communication outlet 64 to nurse call system 70 and/or one or more room devices 72, 74, 76 are possible.

Nurse call cable 66 (FIG. 2) enables linked locator unit 60 to communicate with nurse call system 70 and/or room devices 72, 74, 76. Because patient support apparatus 20 is able to wirelessly communicate with linked locator unit 60, patient support apparatus 20 is thereby able to communicate with nurse call system 70 and room devices 72, 74, 76. A patient supported on patient support apparatus 20 who activates a nurse call control on patient support apparatus 20 causes a signal to be wirelessly sent from patient support apparatus 20 to linked locator unit 60, which in turn conveys the signal via nurse call cable 66 to the nurse call system 70, which forwards the signal to one or more remotely located nurses (e.g. nurses at one or more nurse's stations 78). If the patient activates one or more room device controls on patient support apparatus 20, one or more wireless signals are conveyed to linked locator unit 60, which in turn sends appropriate signals via nurse call cable 66 to communication outlet 64 and the room device 72, 74, 76 that change one or more features of these devices (e.g. the volume, channel, on/off state, etc.).

As is also shown in FIG. 2, patient support apparatus 20 is further configured to communicate with a local area network 80 of the healthcare facility. In the embodiment shown in FIG. 2, patient support apparatus 20 includes a wireless network transceiver 96 (FIG. 3) that communicates wirelessly with local area network 80. Network transceiver 96 is, in at least some embodiments, a WiFi transceiver (e.g. IEEE 802.11) that wirelessly communicates with one or more conventional wireless access points 82 of local area network 80. In other embodiments, network transceiver 96 may be a wireless transceiver that uses conventional 5G technology to communicate with network 80, one or more servers hosted thereon, and/or other devices. In some embodiments, network transceiver 96 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

In some embodiments, network transceiver 96 is a wired transceiver that is adapted to allow patient support apparatus 20 to communicate with network 80 via a wired connection, such as an Ethernet cable that plugs into an Ethernet port (e.g. an RJ-45 style port, an 8P8C port, etc.) built into patient support apparatus 20. In still other embodiments, patient support apparatus 20 includes both a wired transceiver 96 for communicating with network 80 via a wired connection and a wireless transceiver 96 for wirelessly communicating with network 80.

Patient support apparatus 20 is configured to communicate with one or more servers on local area network 80 of the healthcare facility (FIG. 2). One such server is a patient support apparatus server 84. Patient support apparatus server 84 is adapted, in at least one embodiment, to receive data from the patient support apparatuses 20 positioned within the healthcare facility and distribute this data to caregivers, other servers, and/or other software applications. Server 84 may also be configured to receive data from one or more UWB devices 100 that are positioned within one or more volumes of space defined around patient support apparatus 20 and/or within a volume of space defined around locator units 60. Such data is then routed by patient support apparatus server 84 to one or more desired destinations. In some embodiments, the data that is received from one or more UWB devices 100 may include audio signals from a microphone in the user device, and patient support apparatus server 84 may forward those audio signals to an appropriate caregiver device (e.g. a smart phone, a caregiver badge, or other device with audio-playback capabilities).

In some embodiments, the data from the UWB device(s) 100 is forwarded from the device(s) 100 to patient support apparatus 20, and from patient support apparatus 20 to server 84 via network transceiver 96 and one or more access points 82. In other embodiments, such as where a locator unit 60 includes its own network transceiver, the data from a UWB device 100 may be forwarded to the locator unit 60 and the locator unit 60 may then forward the data to server 84 via its network transceiver's communication with one or more of the access point 82. In such embodiments, the UWB device 100 may forward its data directly to the locator unit 60 without sending it to patient support apparatus 20, or it may send its data to patient support apparatus 20 first and patient support apparatus 20 may then forward the data to the locator unit 60. Other manners of routing data from the UWB device 100 to server 84 may be used, and in some embodiments, the device 100 may send some types of data to server 84 along a first route and send other types of data to server 84 along a second and different route.

In some embodiments, patient support apparatus server 84 is configured to communicate at least some of the patient support apparatus data and/or UWB device data received from patient support apparatuses 20 to a remote server 86 that is positioned geographically remotely from the healthcare facility. Such communication may take place via a conventional network appliance 88, such as, but not limited to, a router and/or a gateway, that is coupled to the Internet 90. The remote server 86, in turn, is also coupled to the Internet 90, and patient support apparatus server 84 is provided with the URL and/or other information necessary to communicate with remote server 86 via the Internet connection between network 80 and server 86.

In some alternative embodiments, patient support apparatus 20 may be configured to communicate directly with one or more cloud-based servers, such as remote server 86, without utilizing patient support apparatus server 84. That is, in some embodiments, patient support apparatuses 20 may be configured to communicate directly with a remote server without relying upon any locally hosted servers (e.g. servers hosted on network 80). Patient support apparatus 20 is provided with the URL and/or other information necessary to communicate with remote server 86 via the Internet connection between network 80 and remote server 86. In some such embodiments, network appliance 88 is a router configured to support such direct connections. Still other types of direct-to-cloud connections may be utilized with one or more of patient support apparatuses 20. When patient support apparatus 20 is configured to directly communicate with remote server 86, patient support apparatus server 84 may be omitted and any one or more of the functions of patient support apparatus server 84 described herein may be performed by remote server 86.

Patient support apparatus server 84 is also configured to determine the location of each patient support apparatus 20 (and/or its associated UWB devices), or receive the location of each patient support apparatus 20 (and/or its UWB associated devices) from the patient support apparatuses 20.

In some embodiments, patient support apparatus server 84 determines the room number and/or bay area of each patient support apparatus 20 and its associated UWB devices 100 that are positioned within a room 58, as well as the location of patient support apparatuses 20 and their associated UWB devices 100 that are positioned outside of a room 58, such as those that may be positioned in a hallway, a maintenance area, or some other area. In general, patient support apparatus server 84 may be configured to determine the position of any patient support apparatus 20 that is positioned within communication range of one or more locator units 60, as well as the location of any associated UWB devices 100 that are positioned within one or more volumes of space defined around the patient support apparatus 20.

Patient support apparatus server 84 (FIG. 2) may be adapted to communicate with a plurality of other servers 92, such as a conventional EMR server, a conventional badge server, a conventional Admission, Discharge, and Transfer (ADT) server, and/or a conventional caregiver assignment server. Alternatively, patient support apparatus server 84 may be combined, either partially or wholly, with any one or more of these other servers 92. A typical EMR server stores individual patient records. Such patient records identify a patient by name and include medical information associated with that patient. Such medical information may include all of the medical information generated from the patient's current stay in the healthcare facility as well as medical information from previous visits. It will be understood that the term "EMR server," as used herein, also includes Electronic Health Records servers, or EHR servers for short, and that the present disclosure does not distinguish between electronic medical records and electronic health records.

A typical caregiver assignment server stores data that matches specific caregivers to specific rooms and/or bays within the healthcare facility. The caregiver assignment server stores information regarding shift changes, personnel, and the general assignments of caregivers who are employed by the healthcare facility. In some caregiver assignment servers, caregivers are assigned to specific patients, rather than to specific rooms, in which case the caregiver assigned server may correlate caregivers to individual patients rather than rooms and/or bays. Still further, some conventional nurse call systems may be configured to carry out the functions of the caregiver assignment server, in which case the caregiver assignment server may be replaced by and/or supplemented with a nurse call server.

A typical ADT server stores patient information, including the identity of patients and the corresponding rooms 58 and/or bays within rooms to which the patients are assigned. That is, the ADT server matches specific patients to specific rooms and/or bays within the healthcare facility. The patient's names are entered into the ADT server by one or more healthcare facility staff whenever a patient checks into the healthcare facility and the patient is assigned to a particular room within the healthcare facility. If and/or when a patient is transferred to a different room and/or discharged from the healthcare facility, the staff of the healthcare facility update the ADT server. The ADT server therefore maintains an up-to-date set of data that correlates patient names with their assigned rooms and/or bays. In some conventional electronic medical record systems, the functions of the ADT server may be incorporated into the EMR system, and EMR server may therefore, in some embodiments, carry out the functions of an ADT server.

A typical badge server is configured to manage communications between, and keep track of the locations of, and the specific caregivers assigned to, individual caregiver badges. Such badges are typically worn by healthcare workers, such as caregivers, service technicians, cleaning personnel, transportation assistants, etc. The badge server maintains a set of data that correlates badge IDs with individual healthcare workers. Each badge includes a unique ID that distinguishes that badge from other badges.

In some embodiments, the badges may include UWB transceivers that enable their location within the healthcare facility to be more precisely determined, and/or that enable the badges to perform other functions. Examples of badges that include UWB transceivers and that may be incorporated into the system of the present disclosure are described in greater detail in commonly assigned U.S. provisional patent application Ser. No. 63/356,061 filed Jun. 28, 2022, by inventors Krishna Bhimavarapu et al. and entitled BADGE AND PATIENT SUPPORT APPARATUS COMMUNICATION SYSTEM; in commonly assigned U.S. provisional patent application Ser. No. 63/356,065 filed Jun. 28, 2022, by inventors Jerald Trepanier et al. and entitled BADGE AND PATIENT SUPPORT APPARATUS COMMUNICATION SYSTEM; and in commonly assigned U.S. provisional patent application Ser. No. 63/356,238 filed Jun. 28, 2028, by inventors Madhu Sandeep Thota et al. and entitled BADGE AND PATIENT SUPPORT APPARATUS COMMUNICATION SYSTEM; the complete disclosures of all of which are incorporated herein by reference. The system of the present disclosure may be configured to carry out any of the functions of the patient support apparatuses, patient support apparatus server, badges, and locator units, respectively, disclosed in any of the aforementioned '061, '065, and/or '238 patent applications.

When badges are used with the system of the present disclosure, the badges may be badges of the type sold or marketed by Stryker Corporation of Kalamazoo, Michigan, under the names Vocera Badge, Vocera Smartbadge, and/or Vocera Minibadge. Other types of badges may also, or alternatively, be used. Such badges include the ability to transmit voice communications of healthcare workers to other badges and/or other locations within a healthcare facility. Some of the badges may also include text messaging abilities, alarm notifications, and other functions. When integrated into the system described herein, such badges may be modified to include one or more ultra-wideband transceivers and/or tags that communicate with ultra-wideband transceivers onboard patient support apparatus 20, built into locator unit 60, and/or built into portable communication tool 400, as will be discussed in greater detail herein. In some embodiments, patient support apparatus 20 and/or locator units 60 may be configured to repetitively determine the location of any of the badges that are positioned within range of its ultra-wideband transceivers and determine whether the badge is positioned inside or outside of one or more volumes of space.

It will be understood that the architecture and content of local area network 80 will vary from healthcare facility to healthcare facility, and that the example shown in FIG. 2 is merely one example of the type of network a healthcare facility may be employ. Local area network 80 will typically allow one or more electronic devices 98 to access the local area network 80 and the servers hosted thereon via wireless access points 82. Such electronic devices 98 include, but are not limited to, smart phones, tablet computers, portable laptops, desktop computers, smart televisions, and other types of electronic devices that include a WiFi capability and that are provided with the proper credentials (e.g. SSID, password, etc.) to access network 80 (and, in at least some situations, patient support apparatus server 84). Patient support apparatus server 84 is configured, in some embodiments, to share data with one or more electronic devices 98 that relates to patient support apparatus 20, that relates to one or more UWB devices 100 that become associated with patient support apparatus 20 (or the patient assigned thereto), that relates to one or more badges that become associated with patient support apparatus 20, and/or that relates to one or more medical records of the patient stored in the EMR server.

Linked locator units 60 (FIG. 2) are adapted to wirelessly receive signals from patient support apparatus 20 and deliver the signals to communications outlet 64 in a manner that matches the way the signals would otherwise be delivered to communications outlet 64 if a conventional nurse call cable 66 were connected directly between patient support apparatus 20 and communications outlet 64. Linked locator units 60 are also adapted to transmit signals received from communications outlet 64 to patient support apparatus 20 via a BT transceiver 106 and/or a UWB transceiver 126 (FIG. 3). Thus, patient support apparatus 20 and linked locator unit 60 cooperate to send signals to, and receive signals from, communications outlet 64 in a manner that is transparent to communications outlet 64 such that outlet 64 cannot detect whether it is in communication with patient support apparatus 20 via a wired connection or it is in communication with patient support apparatus 20 via a wireless connection between patient support apparatus 20 and linked locator unit 60 (the latter of which is in wired communication with outlet 64). In this manner, a healthcare facility can utilize the wireless communication abilities of one or more patient support apparatuses 20 without having to make any changes to their existing communication outlets 64.

As noted, in addition to sending signals received from patient support apparatus 20 to communications outlet 64, linked locator units 60 are also adapted to forward signals received from communications outlet 64 to patient support apparatus 20. Linked locator units 60 are therefore adapted to provide bidirectional communication between patient support apparatus 20 and communications outlet 64. This bidirectional communication includes, but is not limited to, communicating command signals from any of control panels 54 and/or from any of electronic devices 98 to corresponding room devices 72, 74, and/or 76 and communicating audio signals between a person supported on patient support apparatus 20 and a caregiver positioned remotely from patient support apparatus 20. The audio signals received by linked locator unit 60 from a microphone on patient support apparatus 20 are forwarded to communications outlet 64 (for forwarding to nurse call system 70), and the audio signals of a remotely positioned nurse that are received at communications outlet 64 (from nurse call system 70) are forwarded to a speaker onboard patient support apparatus 20.

Nurse call cable 66, in some embodiments, includes a conventional 37 pin connector on each end, one of which is adapted to be inserted into outlet 64 and the other one of which is adapted to be inserted into a linked locator unit 60 (or cable port 148 of patient support apparatus 20 if wired communication is desired). Such 37 pin connections are one of the most common types of connectors found on existing walls of medical facilities for making connections to the nurse call system 70 and room devices 72, 74, and 76. Linked locator unit 60 and nurse call cable 66 are therefore configured to mate with one of the most common type of communication outlets 64 used in medical facilities. Such 37 pin connectors, however, are not the only type of connectors, and it will be understood that linked locator units 60 can utilize different types of connectors that are adapted to electrically couple to different types of nurse call cables 66 and/or different types of communication outlets 64. One example of such an alternative communications outlet 64 and cable 66 is disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 64 and corresponding connectors may be utilized.

Locator unit 60 (FIG. 2) also includes an electrical cord 150 having a plug positioned at a far end that is adapted to be inserted into a conventional electrical outlet 108. Electrical cord 150 enables locator unit 60 to receive power from the mains electrical supply via outlet 108. It will be appreciated that, in some embodiments, locator unit 60 is battery operated and cord 150 may be omitted. In still other embodiments, locator unit 60 may be both battery operated and include cord 150 so that in the event of a power failure, battery power supplies power to locator unit 60, and/or in the event of a battery failure, electrical power is received through outlet 108.

In addition to the other functions described herein, locator units 60 are configured to communicate location data to patient support apparatus 20 that enables patient support apparatus 20 and/or patient support apparatus server 84 to determine the location of patient support apparatus 20 within the healthcare facility. In general, such location determination is carried out by patient support apparatus 20 analyzing wireless ultra-wideband (UWB) signals communicated between itself and locator unit 60 in order to determine its position relative to locator unit 60. If patient support apparatus 20, or a predefined reference point on patient support apparatus 20 (e.g. its head end, its center, etc.) is positioned within a threshold distance of locator unit 60, patient support apparatus 20 associates itself with the locator unit 60. When associated, patient support apparatus 20 may communicate data to locator unit 60, receive data from locator unit 60, and also deem its location within the healthcare facility to be the same as location of locator unit 60. When patient support apparatus 20 is outside of the threshold distance, it does not associate itself with locator unit 60, and therefore does not exchange data with locator unit 60 or consider its location to be the same as that of locator unit 60's location.

In some embodiments, patient support apparatus 20 is configured to associate itself with a particular locator unit 60 if controller 140 determines that the locator unit 60 is within a first volume of space defined around patient support apparatus 20, or locator unit 60 determines that patient support apparatus 20 (or a reference point thereon) is positioned within a second volume of space defined around locator unit 60. In other words, in some embodiments, the volume of space is defined with respect to each locator unit 60 and does not move, while in other embodiments, the volume of space is defined with respect to patient support apparatus 20 and moves as patient support apparatus 20 moves. In some embodiments, patient support apparatus 20 associates itself with a nearby locator unit 60 if both the locator unit 60 and the patient support apparatus 20 (or a reference point thereon) are concurrently within a common predefined volume of space. Regardless of whether the volume of space is defined with respect to a locator unit 60, or with respect to a patient support apparatus 20, by at least one or both of these devices (locator unit 60 and patient support apparatus 20) being positioned within the predefined volume of space, the locator unit 60 and patient support apparatus 20 will be positioned within a threshold distance of each other.

After associating itself with a particular locator unit 60, patient support apparatus 20 is configured to be able to have its absolute position within the healthcare facility determined by receiving a unique locator identifier (ID) 122 (FIG. 3) from the locator unit 60. The location of each locator unit 60 in the healthcare facility is surveyed during the installation of locator units 60, and the unique IDs 122 of each locator unit 60 are also recorded during the installation of locator units 60. This surveying information and corresponding ID information may be stored in patient support apparatus server 84 and/or onboard the patient support apparatuses 20, thereby enabling a patient support apparatus 20 and/or patient support apparatus server 84 to determine the location of a patient support apparatus 20 once it is associated with a particular locator unit 60.

In those embodiments where patient support apparatus server 84 is configured to determine the location of patient support apparatus 20, patient support apparatus 20 sends its relative position information with respect to the associated locator unit 60, and/or the ID 122 of the associated locator unit 60 (and its own unique patient support apparatus ID 130 (FIG. 3) to server 84. Server 84 includes a table of all of the locations of the locator units 60 (which, as noted, is generated via a surveying operation during the installation of locator units 60), and it uses that table to correlate the patient support apparatus IDs 130 and the locator unit IDs 122 it receives to specific locations within the healthcare facility. Thus, if a particular patient support apparatus 20 (with a particular ID 130) sends to server 84 an associated locator unit ID 122 that corresponds to room 430, server 84 determines that that particular patient support apparatus 20 is currently located in room 430. Generally speaking, the location of a patient support apparatus 20 is deemed to correspond to whichever locator unit 60 it is currently associated with, and if it is not currently associated with any locator unit 60, its location may be considered to be indeterminate.

In some embodiments of patient support apparatuses 20 and locator units 60, the relative location of a patient support apparatus 20 to a locator unit 60 is determined solely using ultra-wideband communication between the patient support apparatus 20 and the locator unit 60. Alternatively, in some embodiments, patient support apparatus 20 solely uses short range infrared communications with locator unit 60 to determine its relative location, wherein such short range infrared communications are only possible when the patient support apparatus 20 is positioned within a close proximity to the locator unit 60 (e.g. in the range of about 1-3 unobstructed meters). In these latter embodiments, patient support apparatus 20 may report that its location coincides with that of the nearby locator unit 60 when it is able to successfully communicate with the nearby locator unit 60 using these short range infrared communications. Still further, in some embodiments, patient support apparatus 20 and locator unit 60 may communicate with each other using both infrared and ultra-wideband communications. Further details regarding the use of short range infrared communications for location determination are described in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

In some embodiments, locator units 60 and/or patient support apparatuses 20 may be constructed to include any or all of the functionality of the wireless headwall units and/or patient support apparatuses disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; in commonly assigned U.S. patent application Ser. No. 63/206,937 filed May 19, 2020, by inventors Alexander Bodurka et al. and entitled PATIENT SUPPORT APPARATUSES WITH HEADWALL COMMUNICATION; and/or in commonly assigned U.S. patent application Ser. No. 63/245,245 filed Sep. 17, 2021, by inventors Kirby Neihouser et al. and entitled SYSTEM FOR LOCATING PATIENT SUPPORT APPARATUSES, the complete disclosures of all of which are incorporated herein by reference.

Still further, in some embodiments, locator units 60 and/or patient support apparatuses 20 may be constructed to include any of the features and/or functions of the headwall units **144*a*** and/or patient support apparatuses disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference.

FIG. 2 also illustrates a portable communication tool 400 that may be used to communication with, configure, test, troubleshoot, install software, remotely analyze the communications abilities of, and/or perform other communication functions with respect to any of the locator units 60, patient support apparatuses 20, and/or UWB devices 100 that are positioned within a healthcare facility. That is, communication tool 400 allows a user to directly communicate using UWB communications with a nearby locator unit 60, patient support apparatus 20, and/or UWB device 100. Tool 400 may allow the user to change one or more configuration settings on the locator unit 60, patient support apparatus 20, and/or UWB device 100. In addition, communication tool 400 may also read one or more settings on the nearby locator unit 60, patient support apparatus 20, and/or UWB device 100 and display them to the user, as well as perform tests on, send commands to, and/or gather diagnostic information from these UWB devices (20, 60, and/or 100), as will be discussed in greater detail below. Communication tool 400 thereby enables technicians to more easily troubleshoot, configure, and/or test locator units 60, patient support apparatuses 20, and/or UWB devices 100.

In the particular embodiment shown in FIG. 2, communication tool 400 is operated by a technician by coupling it to a portable computer 402. Such coupling may take on any of a variety of different forms, such as wired coupling or wireless coupling. In at least one embodiment, communication tool 400 is coupled to portable computer 402 by a conventional Universal Serial Bus (USB) cable 406, such as is shown in FIG. 2. It will be understood that other types of cables may be used, such as, but not limited to, one or more types of network cables (e.g. CAT 5, CAT 5E, etc.), a Firewire cable, an RS-232 cable, an RS-485 cable, etc. It will also be understood that, in place of a wired cable 406, portable computer 402 may be coupled to communication tool 400 via a wireless connection, such as, but not limited to, a Bluetooth connection, a ZigBee connection, a UWB connection, or, in at least some cases, a WiFi connection.

Portable computer 402 may be any computer that is adapted to execute a software application for communicating with tool 400, such as, but not limited to, a conventional laptop, smart phone, and/or tablet computer. The software application may be written, in at least some embodiments, to be compatible with a Microsoft Windows based operating system, or an Apple IOS operating system, or a Google Android operating system, or still another conventional operating system.

Communication tool 400 is a handheld device that may be carried by an authorized individual to any areas within a healthcare facility in which UWB signal may be present (or desirably present). Communication tool 400 is adapted to perform one or more of the following actions: establish UWB communication links with a nearby locator unit 60, patient support apparatus 20, and/or UWB device 100; read one or more settings stored in the locator unit 60, patient support apparatus 20, and/or UWB device 100 and report them to portable computer 402 for display thereon; send new settings and/or new software to locator unit 60, patient support apparatus 20, and/or UWB device 100 with instructions to install those settings; send test commands, dummy commands, and/or actual commands to locator unit 60, patient support apparatus 20, and/or UWB device 100 that instruct these devices to perform one or more actions; read diagnostic data from the locator unit 60, patient support apparatus 20, and/or UWB device 100; determine the distance between the tool 400 and the UWB transceivers onboard the locator unit 60, patient support apparatus 20, and/or UWB device 100; and/or perform still other functions, as will be described in more detail below.

FIG. 3 depicts a block diagram of patient support apparatus 20, a linked locator unit 60, a UWB device 100, communication tool 400, and network 80. As will be discussed in greater detail below, patient support apparatus 20 is configured to automatically determine the location of one or more locator units 60 and/or devices 100 that either have built-in UWB transceivers or a UWB tag attached to them. In addition, patient support apparatus 20 is configured to automatically carry out certain communications with these UWB devices if they are positioned within a defined proximity to patient support apparatus 20. In some embodiments, if a particular UWB device 100 is positioned within the defined proximity, patient support apparatus 20 automatically associates the UWB device 100 with the patient assigned to patient support apparatus 20 (and/or with patient support apparatus 20 itself), and causes data from that UWB device 100 to be automatically directed to one or more destinations. When the UWB device 100 is positioned outside the defined proximity, patient support apparatus 20 may automatically disassociate itself from the UWB device 100 and, in some situations, terminate communications with the UWB device 100 and/or inform patient support apparatus server 84 of the disassociation.

Linked locator unit 60 (FIG. 3) includes an ultra-wideband transceiver 126, a Bluetooth transceiver 106, a locator unit controller 112, configuration circuitry 114, a television controller 116, a headwall interface 118, a network transceiver 120, a unit ID 122, and, in some embodiments, an infrared transceiver 124. Bluetooth transceiver 106 is adapted to communicate with a Bluetooth transceiver 128 onboard patient support apparatus 20 using RF waves in accordance with conventional Bluetooth standards (e.g. IEEE 802.14.1 and/or any of the standards maintained by the Bluetooth Special Interest Group (SIG) of Kirkland, Washington, USA). In some embodiments, transceivers 106 and 128 utilize Bluetooth Low Energy communications.

Ultra-wideband transceiver 126 is adapted to communicate with one or more ultra-wideband transceivers 132 positioned onboard patient support apparatus 20 and/or one or more ultra-wideband transceivers 158 positioned onboard one or more UWB devices 100. Transceiver 126 is adapted to determine a distance between itself and patient support apparatus 20 and/or a device 100. Alternatively, or additionally, transceiver 126 may be adapted to allow one or more of the UWB transceivers 132 onboard patient support apparatus 20 (or one or more of the UWB transceivers 158 onboard the device 100) to determine their distance(s) from transceiver 126. In other words, one or more location engines may be positioned onboard the patient support apparatus 20, onboard the locator unit 60, onboard the devices 100, and/or onboard server 84.

In some embodiments, transceivers 126, 132, and 158 use time of flight (TOF) computations to determine these distances. In other embodiments, transceivers 126, 132, and 158 178 may utilize other techniques (e.g. time difference of arrival, two-way ranging, angle of arrival, channel state information, etc.) for determining their distances from each other, either in addition to, or in lieu of, TOF computations. In some embodiments, transceivers 126, 132, and 158 may also determine an angle between themselves using angular information derived from antenna arrays positions onboard transceivers 126, 132, and 158, or by using other techniques. The position and orientation of each transceiver 132 onboard patient support apparatus 20 is known and stored in an onboard memory 134 and used to determine the position and orientation of patient support apparatus 20 with respect to the locator unit(s) 60 with which it is communicating. Such position and orientation information may be determined using conventional trilateration and/or triangulation techniques, or other techniques.

In some embodiments, transceivers 126, 132, and 158 are implemented as any of the Trimension™ ultra-wideband modules available from NXP Semiconductors of Austin, Texas. These modules include, but are not limited to, the Trimension™ UWB modules ASMOP1BOON1, ASMOP1COOR1, and/or the ASMOP1CO0A1, that utilize any of the following chips: the NXP SR150, SR100T, SR040, NCJ29D5, and/or the OL23DO chips. Modules manufactured and/or marketed by other companies may also be used, including, but not limited to, the Decawave DWM1000, DWM10001C, DWM3000 modules (available from Decawave of Dublin, Ireland); the Nordic TSG5162 SiP module (available from Tsingoal Technology of Beijing, China); and/or the UWB hub, wand, and/or sensors available from Zebra technologies of Lincolnshire, Illinois. Still other types of UWB modules may be used to implement transceivers 126, 132, and 158.

Locator unit controller 112 is adapted to control the operation of transceivers 126, 106, configuration circuitry 114, TV controller 116, headwall interface 118, network transceiver 120, and, if included, IR transceiver 124 (FIG. 3). When infrared transceiver 124 is included, it may be included to provide backwards compatibility to patient support apparatuses 20 that are not equipped with a UWB transceiver 132. That is, some healthcare facilities may include one or more patient support apparatuses that are not equipped with a UWB transceiver 132, but that do include an IR transceiver that is adapted to communicate with IR transceiver 124. When locator unit 60 includes IR transceiver 124, it is able to communicate its unit ID 122 to such patient support apparatuses via IR transceiver 124, which is a short range transceiver that is configured to only communicate with an adjacent patient support apparatus when the patient support apparatus is nearby (e.g. without about five feet or so). Such an adjacent patient support apparatus 20 then communicates the received locator unit ID 122 along with its own unique ID 130 (FIG. 3) to server 84 which, as noted previously, is able to correlate the locator unit ID 122 to a particular location with the healthcare facility. In this manner, server 84 is able to use locator units 60 determine the location of versions of patient support apparatuses 20 that don't have a UWB transceiver 132, but that do have an IR transceiver.

Headwall interface 118 is adapted to change the electrical state of one or more pins that are in electrical communication with communication outlet 64 (via cable 66). Headwall interface 118 changes these electrical states in response to instructions from controller 112. For example, if the exit detection system 136 of patient support apparatus 20 detects a patient exit, a controller 140 of patient support apparatus 20 sends an exit alert signal to linked locator unit 60 and controller 112 responds by instructing headwall interface 118 to change the electrical state of at least one pin that is used to signal an exit alert (or a generic priority alert) to the nurse call system 70 via communications outlet 64. Additionally, if a device 100, such as a portable exit detection sensor, is associated with patient support apparatus 20 and it detects a patient exit, the exit detection sensor may transmit an exit detection alert signal to patient support apparatus 20, which in turn forwards the exit alert signal to linked locator unit 60, and controller 112 responds by instructing headwall interface 118 to change the electrical state of the same pin or pins that it does in response to receiving an exit detection alert from exit detection system 136.

In some embodiments, headwall interface 118 may be constructed in the same manner as, and/or may include any one or of the functions as, the cable interface 88 described in commonly assigned U.S. patent application Ser. No. 63/193,778 filed May 27, 2021, by inventors Krishna Bhimavarapu et al. and entitled PATIENT SUPPORT APPARATUS AND HEADWALL UNIT SYNCING, the complete disclosure of which is incorporated herein by reference. Alternatively, or additionally, headwall interface 118 may be constructed in the same manner as, and/or may include any one or more of the same functions as, the headwall interface 120 disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference. Linked locator unit 60 may also be configured to perform any of the functions of the headwall units 94 disclosed in the above-mentioned '778 patent application.

Configuration circuitry 114 and TV controller 116 may be configured to perform any of the same functions as, and/or be constructed in any of the same manners as, the configuration circuitry 132 and the TV control circuit 134, respectively, of commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which has already been incorporated herein by reference. Additionally, or alternatively, linked locator unit 60 may be configured to perform any of the functions of the headwall units 144 disclosed in the aforementioned '508 patent application.

Headwall interface 118, television controller 116, and configuration circuitry 114 may be omitted from unlinked locator units 60. This is because unlinked locator units 60 are not adapted to communicate with a communication outlet 64 and these components are designed for communications with outlet 64. Unlinked locator units 60 may also omit (or include) IR transceiver 124. Linked locator units and/or unlinked locator units 60 may optionally include (or omit) network transceiver 120. When included, controller 112 may use network transceiver 120 to communicate with patient support apparatus server 84 (via access points 82 and network 80).

Patient support apparatus 20 includes a controller 140, a memory 134, exit detection system 136, a scale system 144, monitoring system 138, a microphone 146, Bluetooth transceiver 128, one or more UWB transceivers 132, display 52 (which may be part of control panel 54*a*, and/or another control panel 54), network transceiver 96, a nurse call interface 154, and a plurality of additional components that are not shown in FIG. 3. Each UWB transceiver 132 is positioned at a known location on patient support apparatus 20. This known location information is stored in memory 134 and/or elsewhere, and may be defined with respect to any suitable frame of reference that is common to patient support apparatus 20. The known location information may include the spatial relationship between UWB transceivers 132 and/or any other components of patient support apparatus 20. For example, in some embodiments, the known location information includes the spatial relationship not only between UWB transceivers 132, but also the spatial relationships between UWB transceivers 132 and one or more of the following: the head end 38 of patient support apparatus 20, the foot end 40 of patient support apparatus 20, the sides of patient support apparatus 20, a reference point defined on patient support apparatus 20, the floor, and/or other components and/or landmarks of patient support apparatus 20. In some embodiments, this location information is used to determine the orientation of patient support apparatus 20 with respect to one or more walls 62, locator units 60, another patient support apparatus 20, and/or another object or structure within the healthcare facility.

In some embodiments, patient support apparatus 20 includes four UWB transceiver 132, each of which are positioned generally adjacent one of the four corners of patient support apparatus 20. In some such embodiments, the four UWB transceiver 132 are attached to, or positioned near, the four corners of litter frame 28. In other embodiments, the four UWB transceivers 132 are attached to, or positioned near, the four corners of base 22. In some embodiments, each of the four UWB transceivers 132 are attached to the corners of support deck 30. Still other locations of the UWB transceivers 132, as well as different numbers of the UWB transceiver 132, may be incorporated into patient support apparatus 20. In those embodiments of patient support apparatus 20 where one or more of the UWB transceivers 132 are coupled to components of patient support apparatus 20 that are movable (e.g. litter frame 28, which can have its height and orientation changed; or support deck 30 that can have its sections, such as head section 44, pivoted), sensors are included within patient support apparatus 20 that communicate the current position of the movable component to controller 140 so that controller 140 is able to determine the current positions of the UWB transceivers 132 and use those positions when determining the current location of a device, such as a caregiver badge and/or another device 100.

Nurse call interface 154 of patient support apparatus 20 (FIG. 3) includes Bluetooth transceiver 128 and a cable port 148, in some embodiments. Nurse call interface 154 provides an interface for patient support apparatus 20 to communicate with outlet 64 of nurse call system 70. That is, nurse call interface 154 provides the means for patient support apparatus 20 to bidirectionally communicate with communication outlet 64. As has been discussed, in some situations, patient support apparatus 20 uses Bluetooth transceiver 128 to communicate with Bluetooth transceiver 106 of linked locator unit 60, and linked locator unit 60 forwards communications back and forth between outlet 64 and patient support apparatus 20. In other words, in some situations, linked locator unit 60 functions as a communications intermediary between nurse call interface 154 and outlet 64. Alternatively, a nurse call cable 66 may be coupled directly between patient support apparatus 20 and wall outlet 64, thereby avoiding the need to use linked locator unit 60 as a communication intermediary. In such situations, one end of a nurse call cable 66 is plugged into cable port 148 of patient support apparatus 20 and the other end of the cable 66 is plugged directly into outlet 64. Nurse call interface 154 thereby provides patient support apparatus 20 with the ability to communicate either wirelessly or via wired means with the outlet 64.

Patient support apparatus 20 also includes, in at least some embodiments, a microphone 146 (FIG. 3) that is used to detect the voice of the patient when the patient wants to speak to a remotely positioned nurse. The patient's voice is converted to audio signals by microphone 146 and controller 140 is adapted to forward these audio signals to an adjacent communications outlet 64 positioned in wall 62 (FIG. 2). When a cable 66 is coupled between cable port 148 of patient support apparatus 20 and outlet 64, controller 140 forwards these audio signals to outlet 64 via the cable 66. When no such cable 66 extends between patient support apparatus 20 and outlet 64, controller 140 wirelessly forwards these audio signals to the linked locator unit 60 that it is currently associated with (using transceiver 128, or in some embodiments, one of transceivers 132) and controller 112 of linked locator unit 60 forwards these audio signals to outlet 64. As was noted, outlet 64 is in electrical communication with a conventional nurse call system 70 that is adapted to route the audio signals to the correct nurse's station 78, and/or other location. In some embodiments, microphone 146 acts as both a microphone and a speaker. In other embodiments, a separate speaker may be included in order to communicate the voice signals received from the remotely positioned nurse. In some embodiments, the audio communication between patient support apparatus 20 and communications outlet 64 is carried out in any of the manners, and/or includes any of the structures, disclosed in commonly assigned U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT, the complete disclosure of which is incorporated herein by reference.

UWB device 100 includes, at a minimum, a controller 156, a UWB transceiver 158, and a unique ID 166. It will be understood that, depending upon the particular type of UWB device 100 that it is, UWB device 100 may include a plurality of additional components. UWB transceiver 158 is adapted to communicate with the UWB transceivers 132 positioned onboard patient support apparatus 20 so that the position of the UWB device 100 relative to patient support apparatus 20 can be repetitively determined. The UWB transceivers 158 of UWB devices 100 may be the same as all of the other UWB transceivers discussed herein (e.g. UWB transceivers 126, 132). The UWB transceiver 158 of device 100 is further adapted to transmit unique ID 166 of device 100 to patient support apparatus 20 so that patient support apparatus 20 knows which specific device 100 it is communicating with.

Controller 156 of device 100 is adapted to oversee the operation of device 100, process the communications of UWB transceiver 158 with other UWB transceivers (e.g. transceivers 132), respond to the activation of controls on device 100 (if any), and generally oversee the operation of device 100. In some embodiments, UWB device 100 may be any one or more of the following: a conventional smart phone, a conventional tablet computer; another patient support apparatus 20, an infusion pump, a vital sign sensor, an exercise device, a heel care boot, an IV stand and/or pole, a ventilator, a DVT pump, a patient monitor (e.g. a saturated oxygen ($SpO_2$) monitor, an EKG monitor, a vital sign monitor, etc.), a patient positioning device (e.g. a wedge, turning device, pump), an ambient sensor (e.g. air temperature, air flow, light, humidity, pressure, altitude, sound/noise), a mattress 42, a caregiver badge, a portable exit detection sensor, an attachable nurse call device, an incontinence pad or one or more sensors adapted to detect patient incontinence, a Holter device adapted to monitor and record a patient's heart signals, a patient ID tag or bracelet worn by the patient that identifies the patient, a caregiver tag or ID bracelet worn by a caregiver that identifies the caregiver, a patient temperature management device (or associated device, such as a one or more hoses, thermal wraps, etc.), one or more mobility assistance devices that a patient may be expected to use, and/or still other types of UWB devices.

In those embodiments where UWB device 100 may be an infusion pump, patient support apparatus 20 and patient support apparatus server 84 may be configured to carry out any of the functions associated with the infusion pump that are described in commonly assigned U.S. patent application Ser. No. 63/349,369 filed Jun. 6, 2022, by inventors Krishna Bhimavarapu et al. and entitled COMMUNICATION SYSTEM FOR PATIENT SUPPORT APPARATUSES, the complete disclosure of which is incorporated herein by reference. In those embodiments where UWB device 100 may be a portable exit detection sensor, another patient support apparatus, and/or an attachable nurse call button, patient support apparatus 20 and patient support apparatus server 84 may be configured to carry out any of the functions associated with the portable exit detection sensors, nurse call devices, and secondary patient support apparatuses disclosed in commonly assigned U.S. patent application Ser. No. 63/352,061 filed Jun. 15, 2022, by inventors Jerald Trepanier et al. and entitled COMMUNICATION SYSTEM FOR PATIENT SUPPORT APPARATUSES, the complete disclosure of which is incorporated herein by reference.

Controller 140, as well as controllers 112 and 156, may take on a variety of different forms. In the illustrated embodiment, each of these controllers is implemented as a conventional microcontroller. However, these controllers may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 112, 140, and 156 when carrying out the functions described herein, as well as the data necessary for carrying out these functions, are stored in a corresponding memory that is accessible to that particular controller (e.g. memory 134 for controller 140). In some embodiments, controllers 112, 140, and 156 may include and/or work with a microcontroller that is integrated into, or associated with, the UWB transceiver(s) aboard that particular device (e.g. UWB transceivers 126, 132, and 158), and that microcontroller may act as a location engine, either alone or in combination with controller 112, 140, and 156, for determining the locations of the other UWB transceivers with which it is in communication.

Controller 140 of patient support apparatus 20 utilizes UWB transceivers 132 to determine the relative position of patient support apparatus 20 with respect to one or more nearby locator units 60, and/or one or more UWB devices 100. If patient support apparatus 20 is positioned within range of a locator unit 60, its UWB transceivers 132 communicate with the UWB transceiver 126 positioned on that locator unit 60, and the transceivers 132 and 126 exchange signals that enable them to determine the distances between themselves. This distance determination is done for each UWB transceiver 132 positioned onboard patient support apparatus 20 (or for as many as is necessary in order to determine an accurate position of locator unit 60 relative to patient support apparatus 20).

If a device 100 is positioned within range of the UWB transceivers 132 of patient support apparatus 20, the UWB transceiver 158 of the device 100 communicate with the UWB transceivers 132 of patient support apparatus 20 and exchange signals that enable them to determine the distances between themselves. In some embodiments, this distance determination is done for each UWB transceiver 132 positioned onboard patient support apparatus 20 (or for as many as is necessary in order to determine an accurate position of the device 100 relative to patient support apparatus 20).

In some embodiments, the UWB transceivers 126, 132, and 158 may also be configured to determine an angular relationships between themselves. The distance (and angle information) in at least some embodiments is calculated by UWB transceiver 132 and/or controller 140 of patient support apparatus 20. In other embodiments, one or more of the other UWB device 60, 100 may also, or alternatively, calculate the distance (and angle information) and forward the results of this calculation to patient support apparatus 20 (either via a UWB transceiver or BT transceiver). In either situation, patient support apparatus controller 140 is informed of the distances (and, in some embodiments, as noted, the angle information) between its UWB transceivers 132 and those onboard the nearby device(s) 60 and/or 100. These distances and orientations are then used to calculate a relative position of patient support apparatus 20 to these devices (locator unit 60, device 100) in a common frame of reference that may be defined in a fixed relationship to the patient support apparatus 20 or the device.

Although FIGS. 2 and 3 only illustrate a single locator unit 60, it will be understood that a typical healthcare facility will include multiple locator units 60 positioned at different locations throughout the facility, including ones positioned within patient rooms and others positioned outside of patient rooms. Typically, at least one locator unit 60 will be positioned in each patient room of the healthcare facility, and if the patient room is intended to be occupied by more than one patient (e.g. it includes multiple bays), then additional locator units 60 may be included so that each patient support apparatus 20 will have a locator unit 60 positioned adjacent to each bay area in the room. Additional locator units 60, such as unlinked locator units 60*a*, may also be positioned at other locations through the healthcare facility.

The location of patient support apparatus 20 relative to locator units 60 and/or UWB devices 100 is repetitively determined by an exchange of signals between their UWB transceivers 126, 132, and 158. This exchange is initiated by an interrogation signal that may be sent by the UWB transceivers 126 of one or more of these UWB devices (20, 60, and/or 100). The trigger for sending these interrogation signals (from either source) may simply be the passage of a predefined interval of time, in at least some embodiments. That is, in some embodiments, patient support apparatus 20, locator units 60, and/or devices 100 may be configured to periodically send out an interrogation signal that will be responded to by any UWB transceivers that are positioned with range of that signal. In those embodiments where patient support apparatuses 20 are configured to send out such an interrogation signal, the time intervals between the interrogation signals may be varied depending upon the location and/or the number of devices 100 that are positioned within range of patient support apparatus 20, and/or the status of the patient support apparatus 20. For example, in some embodiments, controller 140 may be configured to send out the interrogation signals with longer timer intervals between them when the patient support apparatus is stationary (and, in some cases, when no devices 100 are currently positioned in communication range), and to send out the interrogation signals with shorter time intervals between them when the patient support apparatus 20 is in motion and/or when at least one device 100 is currently positioned within communication range of transceivers 132. In any of the aforementioned embodiments, motion of the patient support apparatus 20 may be detected in any suitable manner, such as by including one or more motion sensors on the patient support apparatus 20 (e.g. one or more accelerometers), and/or by monitoring the values of the repetitive distance measurements and looking for changes indicative of movement.

In some embodiments, the UWB transceivers of each UWB device 20, 60, and 100 are configured to act as either UWB anchors or as UWB tags. In at least one embodiment, the UWB transceivers 126 of locator units 60 and the UWB transceivers 158 of devices 100 are configured to all act as UWB tags, while the UWB transceivers 132 of patient support apparatus 20 are configured to act as UWB anchors. It will be understood that modifications to these roles of anchors and tags can be made. For example, in some embodiments, the UWB transceivers 132 of patient support apparatus 20 may be modified to act as UWB anchors in some instances and as UWB tags in other instances. Still other modifications can be made.

In general, when a UWB transceiver is configured to act as a UWB tag, it is configured to periodical transmit a UWB start packet, which acts as a discovery packet. The start packet requests that any UWB anchors that are within communication range to respond. If another UWB transceiver that is acting as a UWB tag happens to receive the start packet from another UWB tag, that UWB transceiver is configured to not respond to it. In other words, tags transmit start packets, but do not respond to start packets. UWB anchors, on the other hand, do not transmit start packets, but instead respond to start packets with a response packet that may be referred to as a stamp packet. Anchors therefore transmit stamp packets, but do not transmit start packets. UWB anchors also do not respond to other stamp packets that they may detect from other UWB anchors. In response to receiving a stamp packet from a UWB anchor, the UWB tags are configured to transmit an end packet back to the UWB anchor that transmitted the stamp packet.

The combination of the start, stamp, and end packet generally defines a ranging session between a UWB anchor and a UWB tag. The ranging session uses time of flight (TOF) information generated from the start, stamp, and end packets to allow the anchor and/or tag to determine a distance between the tag and the anchor. In some embodiments, the start, stamp, and/or end packet may also contain other data in their payloads that is used for other purposes besides ranging. From the ranging information, the distance between the anchor and tag is determined. These ranging sessions are repetitively carried out while a UWB anchor and UWB tag are within communication range.

In some embodiments, the time interval between ranging sessions is controlled by the UWB tag. That is, after the UWB tag sends a start packet, receives a stamp packet in response, and sends an end packet in response to the stamp packet, the UWB tag is configured to wait a defined amount of time before sending out another start packet. The defined amount of time is programmed into the UWB tag and can be varied during operation of the UWB tag. In some embodiments, the UWB tag may be configured to change this defined amount of time (hereinafter, the "ranging interval") based upon whether the UWB device with the tag is associated with, or not associated with, a UWB device having an anchor. In other embodiments, the ranging interval may be changed by a tag based upon the status of one or more of the UWB devices that are involved in the ranging session. Such status may include, but is not limited to, the movement status of one or more of the UWB devices, the position and/or state of one or more components of the devices, the location of the UWB device within the healthcare facility and/or in relation to other UWB device(s), and/or other factors.

After the installation of locator units 60 in a particular healthcare facility, the location of each locator unit 60 within that facility is recorded. In some embodiments, the coordinates of the locations of locator units 60 are recorded in a common frame of reference (or converted to a common frame of reference after recordation). Such coordinates may be three dimensional (i.e. include a vertical and two horizontal components), or they may be two dimensional (no height component). In other embodiments, a more generalized location of one or more locator units 60 is determined, rather than the precise coordinates of the locator units 60. The generalized location of the locator units 60 may include an indication of the room, bay, area, hallway, portion of a hallway, wing, maintenance area, etc. that the locator unit 60 is positioned in. In still other embodiments, the locations of one or more locator units 60 are determined both generally and more precisely.

Regardless of how the location of each locator unit 60 is initially determined after they are installed in a healthcare facility (e.g. whether their coordinates are determined or a more generalized location is determined), the locations of all of the locator units 60, as well as their unique IDs 122, are stored in a memory accessible to server 84. Server 84 then uses this location data and ID data to determine the location of a patient support apparatus 20 (as well as the location of associated devices 100). Alternatively, or additionally, the location data and IDs 122 are forwarded to patient support apparatuses 20 for storage in their onboard memories 134 and for use in determining their own locations. In some embodiments, the location of each locator unit 60 (whether specific and/or general) may also, or alternatively, be stored in a memory within that particular locator unit 60 and shared with the devices it communicates with (e.g. patient support apparatuses 20). In some other embodiments, the location of each locator unit 60 may be stored in multiple locations.

For all of the UWB devices 100 that patient support apparatus 20 is configured to determine the location of (i.e. perform UWB ranging with), controller 140 of patient support apparatus 20 uses the relative position information to determine how it will interact with these devices 100, including whether to associate with these devices or not. When controller 140 associates patient support apparatus 20 with one or more of these devices, as will be discussed in greater detail below, controller 140 and/or server 84 may take one or more of the following actions: display data from these devices on display 52 and/or another display device; automatically route data from one or more of these devices to one or more appropriate destinations, and/or take other actions.

As discussed above, for locator units 60, controller 140 is configured to determine whether to automatically associate patient support apparatus 20 with a particular locator unit 60 based on whether both locator unit 60 and patient support apparatus 20 (or a reference point thereon) are positioned within a common volume of space. For devices 100, controller 140 is configured to determine whether to automatically associate patient support apparatus 20 with a particular device 100 based on whether the device 100 is positioned within a predetermined volume of space that surrounds the patient support apparatus 20. The predetermined volumes of space(s) used for associating/disassociating a locator unit 60 with patient support apparatus 20 may be of different sizes, shapes, and/or volumes than the predetermined volume of space(s) used for associating/disassociating a UWB device 100 with patient support apparatus 20.

Once a device—locator unit 60 or UWB device 100—is associated with patient support apparatus 20, it thereafter remains associated with patient support apparatus 20 until it moves outside of the corresponding predetermined volume of space, at which point controller 140 disassociates the device from patient support apparatus 20. That is, controller 140 repetitively determines and monitors the position of the UWB devices (60, 100) while they are within UWB communication range, and if a device moves outside of a corresponding volume of space, controller 140 automatically disassociates the device from patient support apparatus 20.

In some embodiments, controller 140 may use modified volumes of space—such as, but not limited to, larger space volumes—when determining whether to automatically disassociate devices from patient support apparatus 20. In other words, once a device—locator unit 60 or device 100—has been determined to be positioned inside of a particular volume of space (and any additional association conditions are met, if there are any), and controller 140 has associated the device with patient support apparatus 20, controller 140 may thereafter increase the size of—and/or otherwise change one or more dimensions of—the volume of space when determining whether to automatically disassociate the device from patient support apparatus 20. In this manner, the volumes of space may have a sort of hysteresis aspect wherein a device has to be positioned inside of a smaller space volume in order to be associated with patient support apparatus 20, but thereafter can only be disassociated if it moves outside of a larger sized volume of space. One example of this type of hysteresis effect is shown in FIG. 12 of commonly assigned U.S. patent application Ser. No. 63/356,242 filed Jun. 28, 2022, by inventors Madhu Sandeep Thota et al. and entitled PATIENT SUPPORT APPARATUS COMMUNICATION AND LOCATION SYSTEM, the complete disclosure of which is incorporated herein by reference. Controller 140 may be configured, in some embodiments, to utilize the hysteresis effect disclosed in the aforementioned '242 application, and/or to implement any of the functions of the patient support apparatuses disclosed therein. In still other embodiments, controller 140 may use the same dimensions for the volumes of space for both association and disassociation purposes.

Communication tool 400 (FIGS. 2-3) is configured to allow a user to determine which UWB transceivers 126, 132, and/or 158 are currently present and within communication range of communication tool 400. Communication tool 400, in some embodiments, is configured to act both as a UWB anchor and as a UWB tag, and to automatically range with whatever UWB device(s) (patient support apparatus 20, locator unit 60, and/or UWB devices 100) that are currently within UWB range of communication tool 400.

In the embodiment shown in FIG. 3, communication tool 400 includes a controller 410, a UWB transceiver 412, a Bluetooth transceiver 414, and a transceiver 416. Tool 400 may also include additional structures not shown in FIG. 3 such as, but not limited to, one or more indicators and/or additional circuitry for carrying out additional functions. UWB transceiver 412 is configured to communicate with UWB transceivers 126, 132, and 158 when they are positioned within UWB range of tool 400. Bluetooth transceiver 414 is configured, in some embodiments, to communicate with Bluetooth transceiver 106 onboard locator unit 60 and/or Bluetooth transceiver 128 onboard patient support apparatus 20. Transceiver 416 is configured to communicate with computer 402 and, in some embodiments, may be a USB transceiver, a WiFi transceiver, or another transceiver. In some embodiments, transceiver 416 may be omitted and Bluetooth transceiver 414 and/or UWB transceiver 412 may be used to communicate with computer 402. Computer 402 may be a conventional computer and therefore may include a number of additional components, such as, but not including, a keyboard, a mouse, a display 404, one or more coprocessors, additional ports (e.g. a network port, additional USB ports, an HDMI port, headphone and/or microphone jack, etc.), and any other components that are typically found on conventional portable computers. When computer 402 is implemented as a smart phone, it may include a touch screen, a SIM card, and/or other components conventionally found in smart phones.

UWB transceiver 412 may be constructed in the same manner as any of the UWB transceivers previously described herein (e.g. UWB transceivers 126, 132, and/or 158). Controller 410 oversees the operation of communication tool 400 and, in some embodiments, may be a conventional microcontroller. However, controller 410 may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 410 when carrying out the functions described herein, as well as the data necessary for carrying out these functions, are stored in a memory onboard tool 400 (not shown). In some embodiments, controller 410 may include and/or work with a microcontroller that is integrated into, or associated with, UWB transceiver 412, and that microcontroller may act as a location engine, either alone or in combination with controller 410, for determining the locations of the other UWB transceivers with which it is in communication.

Controller 410 may be configured to control UWB transceiver 412 such that it acts both as a UWB tag and as a UWB anchor. That is, controller 410 may be configured to control UWB transceiver 412 to act as a UWB anchor that listens for start packets broadcast by UWB tags (e.g. locator unit 60 and/or UWB devices 100) that are positioned within range of tool 400. In response to such start packets, UWB transceiver 412 is configured to respond with a stamp packet and to carry out a ranging session with each of the UWB tag(s) that broadcast the start packet. The UWB tags may then respond to with an end packet. From these ranging session, controller 410 is able to determine the distance to each and every one of the locator units 60 and/or UWB devices 100 that are positioned within range of tool 400 because, as noted, locator unit 60 and UWB devices 100 may be configured as UWB tags that periodically broadcast (e.g. multiple times a second) a start packet.

In order for communication tool 400 to range with UWB transceivers 132 that are positioned onboard a patient support apparatus 20 and that, as noted, are configured to act as UWB anchors in some embodiments, controller 410 is configured to periodically change UWB transceiver 412 from an anchor mode to a tag mode. In those embodiments of patient support apparatus 20 where UWB transceiver 132 are configured to act as anchors, the UWB transceivers onboard patient support apparatus 20 will respond to the start packet broadcast from tool 400 with a stamp packet. Tool 400, in turn, will respond to the stamp packet with an end packet. UWB transceiver 412 will therefore range with each of the UWB transceivers 132 onboard patient support apparatus 20 and determine the distance between each UWB transceiver 132 and UWB transceiver 412.

Communication tool 400, by periodically switching UWB transceiver 412 between an anchor mode and a tag mode, will therefore be able to range with all UWB tags and anchors that are positioned within communication range of tool 400. Various information about the UWB transceivers 126, 132, and/or 158 that tool 400 is able to range with then be detected and displayed by tool 400 (such as by sending the data to be displayed to computer 402, which displays the data on its display 404). The information that is exchanged during, or after, these ranging sessions will now be described in more detail.

FIG. 6 illustrates several examples of the types of data that may be communicated from one or more UWB devices 20, 60, and/or 100 to communication tool 400 and displayed by tool 400 (e.g. on display 404 of computer 402). This data includes a unique ID 300 of the UWB transceiver 126, 132, and/or 158; a type of product 302 to into which the UWB transceiver is built, a make 304 of the product, a brand name or model name 306 of the product, an internal location 308 of the UWB transceiver, the current signal strength 310 of the UWB signals being detected from the UWB transceiver, a listing 312 of the last set of UWB transceivers that the UWB transceiver has ranged with, a set of recent errors 314, and the current distance 316 between UWB transceiver 412 of tool 400 and the corresponding UWB transceiver.

In the case of locator unit 60, the unique ID 300 of each UWB transceiver corresponds to unit ID 122 (FIG. 3) of the locator unit 60. In the case of a UWB device 100, the unique ID 300 corresponds to the unique device ID 166 of the UWB device 100. In the case of patient support apparatuses 20, each UWB transceiver 132 has a unique ID associated with it (not shown), and unique ID 300 corresponds to those unique IDs. Tool 400 is configured to determine a number of attributes of each UWB transceiver based on the unique ID 300 and/or on other information provided by the UWB transceiver. In some embodiments, controller 410 is configured to determine the product type 302, the make 304, the model 306, and/or the internal location 308 of each UWB transceiver based on the unique ID 300. That is, each unique ID 300 includes a number of characters (numbers, letters, symbols, etc.) that are specific to a particular product type 302, make 304, model 306, and/or location 308. Controller 410 reads the content of unique ID 300 and determines these attributes 302, 304, 306, and/or 308 from the unique ID 300.

In the case of patient support apparatuses 20, which may have more than one UWB transceiver 132 positioned onboard, each patient support apparatus 20 is built such that the UWB transceivers 132 that are positioned in a particular area will always have the same UWB ID 300. For example, if there are four UWB transceiver 132 onboard patient support apparatus 20, each patient support apparatus 20 may be built such that the left head end UWB transceiver 132 has the same unique ID 300 (e.g. QZT433); each left foot end UWB transceiver 132 has the same unique ID 300 (e.g. QZT432); each right head end UWB transceiver 132 has the same unique ID 300 (e.g. QZT431); and each right foot end UWB transceiver 132 has the same unique ID 300 (e.g. QZT430). If there are a different number of UWB transceiver 132 and/or the UWB transceiver 132 are positioned in different locations, a different number of unique IDs 300 may be used with the UWB transceivers 132 and/or different location descriptions may be used. For those devices that only include a single UWB transceiver (e.g. locator units 60 and some UWB devices 100), the unique ID 300 may omit an indication of the location of the UWB transceiver and/or tool 400 may simply list the location in a generic manner (e.g. "center").

In addition to determining the type of product 302 that a particular UWB transceiver is built into, the make 304, the model, 306, and the location 308 of the UWB transceiver, controller 410 of tool 400 may also measure the signal strength 310 of the UWB signals it is receiving from the UWB transceivers it is currently in communication with. Although FIG. 6 depicts the signal strength as being measured in decibels, it will be understood that the signal strength may be measured in other manners (e.g. decibels per milliwatt (dBm), decibels per watt, etc.).

Controller 410 of tool 400 is also configured to retrieve from each UWB transceiver a list 312 of the last UWB transceivers that that particular UWB transceiver previously ranged with. In some embodiments, the list refers to the last twenty UWB transceivers that a particular UWB transceiver ranged with. It will be understood that the list 312 may be comprised of a set of UWB transceivers that is smaller or larger than a set of twenty. In the sample shown in FIG. 6, UWB transceiver QZT433 of a patient support apparatus 20 has previously ranged with only a single UWB transceiver, AFR122, which corresponds to a UWB transceiver 126 incorporated into a locator unit 60. In some embodiments, controller 410 may retrieve not only a list 312 of previously ranged UWB transceivers, but also time stamps for each of the previous ranging sessions so that the user of tool 400 can see not only what UWB devices a UWB transceiver has ranged with, but also the time when such ranging sessions occurred.

As shown in FIG. 6, controller 410 of tool 400 may also retrieve any errors 314 that were detected for each UWB transceiver it is in communication with. In some embodiments, controller 410 is configured to interpret the error codes 314 and display on display 404 a translation of the error codes. In other embodiments, controller 410 may merely display the error codes without an explanation of what the codes refer to.

Controller 410 is also configured to use the ranging sessions between its UWB transceiver 412 and the other UWB transceivers (126, 132, and/or 158) to determine the distance between these other UWB transceivers and UWB transceiver 412. This distance 316 is shown in the far right column in FIG. 6. Controller 410 may be configured to update these distance measurements multiple times a second, or at another frequency. By displaying these measured distances, a technician can use a tape measure, or other manual tool, to measure these distances to check to see whether the UWB measurements between UWB transceivers are accurate or not.

In addition to, and/or in lieu of any of the data shown in FIG. 6, controller 410 of tool 400 may be configured to retrieve diagnostic information from any of the UWB device (s) it is in communication with (e.g. patient support apparatus 20, locator unit 60, and/or other UWB devices 100). Controller 410 may also or alternatively retrieve the currently software installed on any of the UWB devices it is in communication with. Any of the information retrieved by tool 400 from any of the UWB devices it is in communication with may then be displayed by controller 410 on display 404 (or 404*a*), recorded in a memory of tool 400 (not shown), and/or forwarded to another device (e.g. a computer on network 80).

In some embodiments, controller 410 may be configured to record all UWB traffic it detects and store it in a memory accessible to controller 410. A user of tool 400 may subsequently retrieve this UWB traffic for analysis and/or for troubleshooting purposes. In some embodiments, the UWB traffic may be recorded in a text file, although other file formats may be utilized.

In some embodiments, tool 400 is configured to allow a user to walk through areas of the healthcare facility and detect UWB dead spots. That is, tool 400 may include one or more controls that, when activated by the user, cause tool 400 to provide an indication whenever it is not able to communicate with a UWB device (e.g. locator unit 60, UWB device 100, and/or patient support apparatus 20). The indication may be aural, visual, and/or both. Tool 400 may therefore be used to detect areas of a healthcare facility where locator units 60 are not able to be detected, and/or areas where a patient support apparatus 20's, or UWB device 100's, UWB signals are not detectable.

In some embodiments, tool 400 is configured to allow a user to send test commands to a UWB device (e.g. locator unit 60, UWB device 100, and/or patient support apparatus 20) that it is currently in communication with. Such test commands may mimic any of the commands that these devices generate in response to a particular control, or set of controls, on the user interface(s) of these devices; and/or they may mimic any of the commands that these devices are configured to receive from other sources besides communication tool 400. Thus, for example, in some embodiments, tool 400 may be configured to send an exit detection signal to locator unit 60 that mimics the signal patient support apparatus 20 is configured to send to locator unit 60 when its onboard exit detection system 136 detects a patient exit. By sending such a test command, the user of tool 400 can see how a UWB device will respond to an actual command without having to generate the actual conditions that result in an actual command.

In some embodiments, tool 400 is configured to send any of the test commands and/or other commands to patient support apparatus 20 and/or locator unit 60 that the portable configuration tool 400 is able to send to the patient support apparatuses 20 and/or the headwall units 144 disclosed in commonly assigned U.S. patent application Ser. No. 17/559,374 filed Dec. 22, 2021, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference. Alternatively, or additionally, tool 400 may be configured to send any of the test commands and/or other commands that the service tool 94 is able to send to patient support apparatuses 20 and/or the headwall units 58 disclosed in commonly assigned PCT patent application number PCT/US2022/026437 filed Apr. 27, 2022, by inventors Frank Lee et al. and entitled WIRELESS SERVICE TECHNOLOGY FOR PATIENT SUPPORT APPARATUSES, the complete disclosure of which is also incorporated herein by reference. The test commands, or other commands, that communication tool 400 is configured to send to locator unit 60, patient support apparatuses 20, and/or other UWB devices 100 may be sent by using UWB transceiver 412 and/or by using Bluetooth transceiver 414.

In some embodiments, tool 400 may be configured to send software updates to any of the UWB devices (20, 60, and/or 100) that it is adapted to communicate with. The software updates may refer to the software that is only executed by the recipient UWB transceiver (and its associated controller), and/or it may refer to software updates that are used by the entire device and/or non-UWB components of the device. For example, in some embodiments, tool 400 may be configured to send software updates to patient support apparatus 20 that change the operational characteristics of only one or more of its UWB transceivers 132, and/or it may be configured to send software updates to patient support apparatus 20 that change the overall operation of patient support apparatus 20 (e.g. updates to what is displayed on display 52; updates to the scale system 144, etc.). The software updates may be transmitted using UWB transceiver 412 and/or by using Bluetooth transceiver 414.

In some embodiments, the commands that tool 400 is configured to send to a particular UWB device (20, 60, and/or 100) include a command for the recipient device to identify itself in a visually apparent manner so that the technician using tool 400 can be sure what device each UWB transceiver is integrated into. For example, in some embodiments, tool 400 may be configured to allow a user to send a command to a particular patient support apparatus 20 that causes the patient support apparatus 20 to illuminate one or more lights, to emit one or more sounds, and/or display certain information on display 52. This enables the user of tool 400 to more easily confirm which devices correspond to which UWB transceivers, particularly in areas where they may be patient support apparatuses 20. Similar commands may be sent by tool 400 to locator units 60 and/or other UWB devices 100 so that the technician can more easily distinguish one of these devices from other one(s) that may happen to also be positioned within range of tool 400 at that moment.

Tool 400 is configured to display the data shown in FIG. 6, as well as other data. In the embodiment of tool 400 shown in FIGS. 2 and 3, tool 400 displays this data on a display 404 of a coupled computer 402. In other embodiments, tool 400 may be configured to include its own display. Still further, in some embodiments, such as the embodiment shown in FIGS. 4 and 5, tool 400 may be integrated into a conventional electronic device, such as a smart phone, tablet computer, or other device that has inherent UWB communication abilities.

Figure 4:
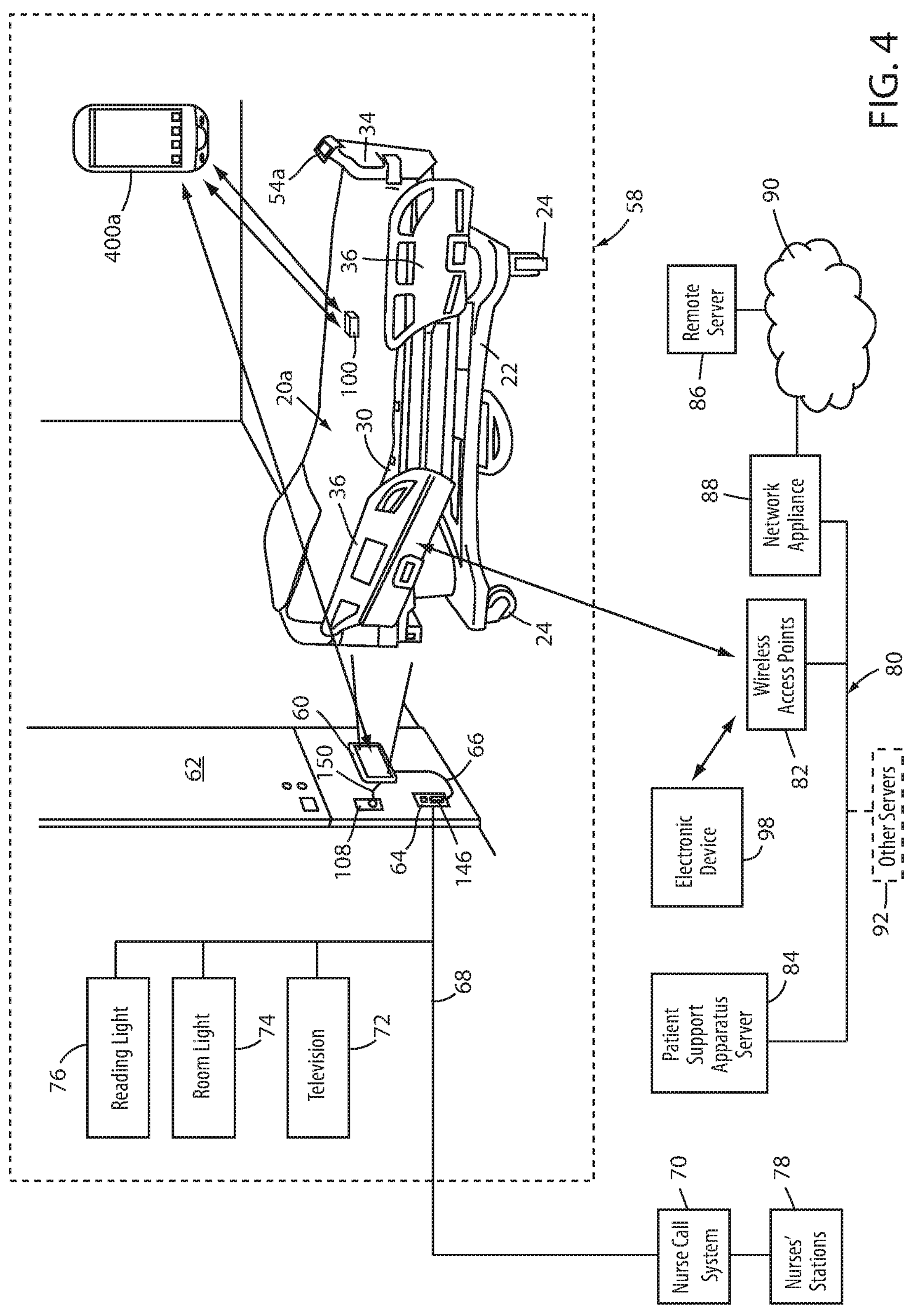
FIG. 4 is a diagram of the patient support apparatus of FIG. 1, a locator unit, a second portable communication tool, and as an example of the IT infrastructure of a typical healthcare facility.
Figure 5:
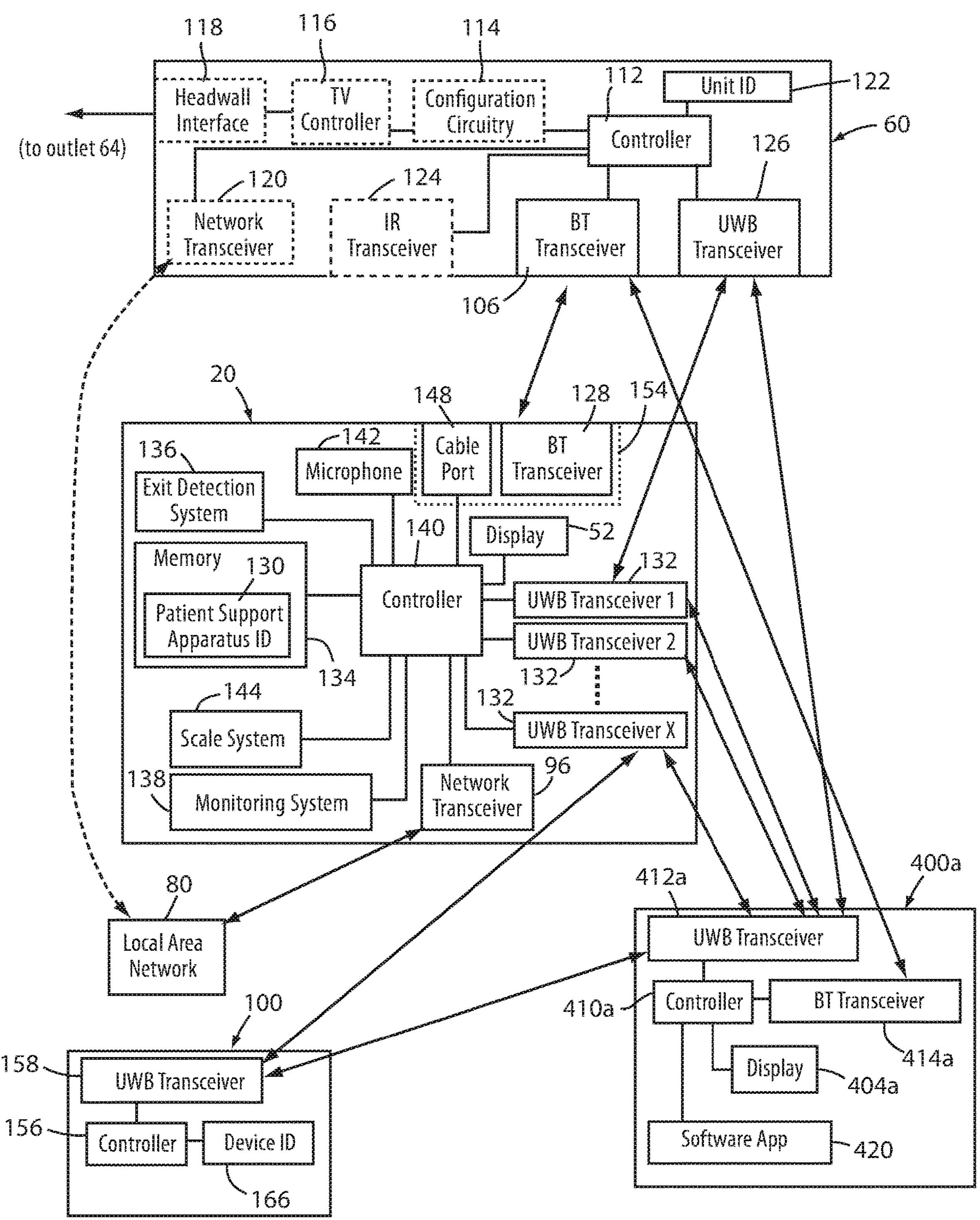
FIG. 5 is a block diagram of the patient support apparatus, locator unit, and second communication tool of FIG. 4.

Tool 400*a* of FIGS. 4 and 5 comprises a software application 420 that is adapted to be executed by a conventional computing device, such as a computer, smart phone, tablet computer, etc. That is, the physical components of tool 400*a* may be all be parts of a conventional computing device that is adapted to execute a specialized software application 420. Software application 420 is configured to control the components of the conventional computing device in the same manner as discussed herein. These conventional computing device components may include a controller 410*a*, a UWB transceiver 412*a*, a Bluetooth transceiver 414*a*, a display 404*a*, and/or other components. Tool 400*a* is configured to carry out any and all of the same functions previously described with respect to tool 400. Instead of sending data to be display to a separate computer 402, however, tool 400*a* sends data to be displayed on its own internal display 404*a*. Tool 400*a*, like tool 400, however, can be configured to send any of the data it gathers to still other devices, such as server 84, and/or other devices in communication with network 80. It will be understood that any and/or all of the aforementioned functions of tool 400 may be integrated into tool 400*a*. It will also be understood that all further references to tool 400 made below will be equally applicable to tool 400*a*, and that tool 400 can be implemented as a device that connects to a computer, or it may be a software application that is installed on a conventional computer, such as a smart phone, laptop, tablet, or other portable computer.

Figure 7:
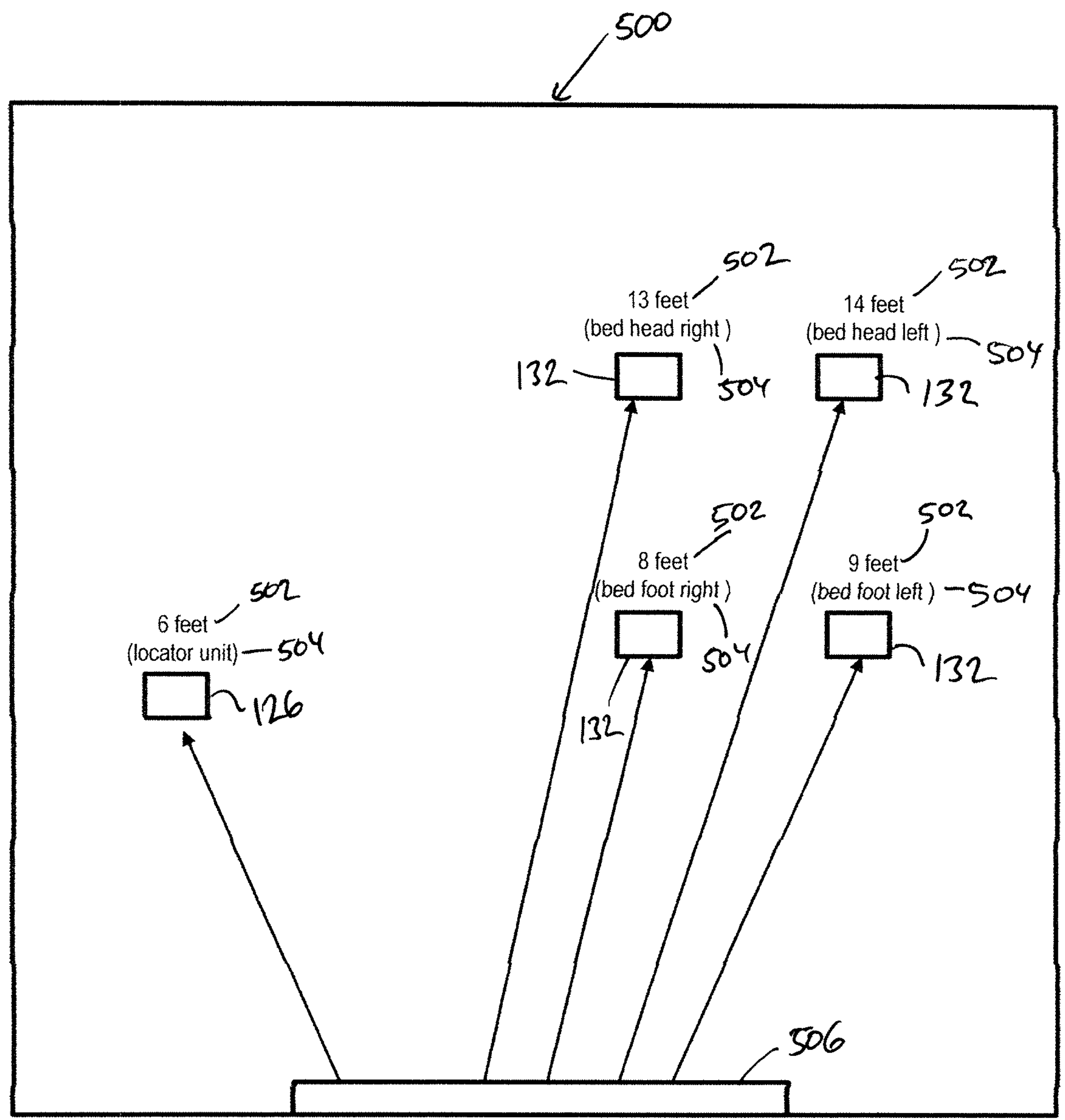
FIG. 7 is an example of a location screen that may be displayed upon a display of the portable communication tool and/or a display in communication with the portable communication tool.

In some embodiments, tool 400 may be configured to display a location screen, such as the location screen 500 shown in FIG. 7. It will be understood, of course, that tool 400 may make variations to the example shown in FIG. 7 and may additionally, and/or alternatively, display other location information. Whether screen 500 and/or other location information is displayed, controller 410 of tool 400 is configured to display such location information on display 404 and/or display 404*a*. In some embodiments, tool 400 may be configured to display screen 500 on still other displays (e.g. display 52 of patient support apparatus 20).

Location screen 500 shows the location of the individual UWB transceivers that are within range of tool 400, whether those UWB transceivers are integrated into a patient support apparatus 20, a locator unit 60, and/or another type of UWB device 100. In the example shown in FIG. 7, screen 500 includes one UWB transceiver 126 built into a locator unit 60 and four UWB transceivers 132 that are built into a patient support apparatus 20. Controller 410 is configured to not only display these UWB transceivers, but to also provide a distance measurement 502 and a descriptor 504. The distance measurement 502 indicates the current distance between tool 400 and the corresponding UWB transceiver (e.g. transceiver 126 is six feet away from the portable tool 400 in FIG. 7). The descriptor 504 provides a short textual description of the particular UWB transceiver that it is associated with. For patient support apparatuses 20 that include multiple UWB transceivers 132, the descriptor 504 indicates where those UWB transceivers 132 are located on the patient support apparatus 20 (e.g. head right, head left, foot left, foot right, etc.).

Controller 400 is configured—either through its own built in software of tool 400 or through software app 420 for tool 400*a*—to update the location of each of the UWB transceivers displayed on screen 500 as the portable tool 400 is moved and/or has its orientation changed. That is, screen 500 displays the location of each UWB transceiver that tool 400 detects in a visual manner that corresponds to where the UWB transceivers would be located from the standpoint of a user who is located at the tool 400 and facing in the same direction that tool 400 is pointing. In the illustrated embodiment, screen 500 includes a tool icon 506 that provides a visual representation of where tool 400 is currently located, as well as it current orientation, relative to the UWB transceivers displayed on screen 500. In other words, tool icon 506 visually indicates the location of tool 400 on screen 500 and shows the UWB transceivers that are positioned in front of tool 400. Thus, for example, in the example of FIG. 7, tool 400 is pointed generally forward with the UWB transceiver 126 of a locator unit 60 position six feet ahead and slightly to the left, while the four UWB transceivers 132 of patient support apparatus 20 are positioned about eight to fourteen feet ahead and just to the right. By looking at screen 500, a user of tool 400 is able to visually see where the UWB transceivers are currently located with respect to the tool 400. As tool 400 is moved and/or rotated, the positions of the UWB devices on screen 500 is automatically updated by controller 410.

Controller 410 is configured, in some embodiments, to determine the distance to each UWB transceiver displayed on screen 500 by ranging its UWB transceiver 412 with the UWB transceivers it detects. This ranging results in a distance measurement. In order to determine the relative orientation of tool 400 to the UWB transceivers it detects, tool 400 may include additional UWB transceivers 412 that are positioned at known positions on tool 400 and that each range with the detected UWB transceivers (e.g. 126, 132, and/or 156). From this multiple ranging, controller 410 is able to determine the relative orientation (and position) between tool 400 and the UWB transceivers it detects. Alternatively, or additionally, tool 400 may determine the relative orientation of itself to the UWB transceivers it detects using directional antennas that are part of the UWB transceivers it detects and/or its own UWB transceiver 412.

In some embodiments, controller 410 is configured to determine the relative orientation of the UWB transceivers it detects (e.g. 126, 132, and/or 156) by instructing patient support apparatus 20 to use its UWB transceivers 132 to determine the relative position and orientation of patient support apparatus to all of the UWB transceivers that UWB transceivers 132 can detect, including UWB transceiver 412 onboard tool 400. Because patient support apparatus 20 includes multiple UWB transceivers 132 positioned at known locations with respect to each other, it is able to use multiple ranging sessions and/or conventional triangulation techniques to determine the relative position and orientation of itself with respect to any other UWB transceivers 126, 158, and/or 412 that it detects. Once it determines these positions and orientations, controller 140 sends this information to tool 400 and controller 140 displays it on its display, such as in the manner shown in FIG. 7. Portable tool 400 may also include a compass, one or more accelerometers, and/or other sensors for determining its orientation relative to patient support apparatus 20 and/or other UWB devices and/or to the room, or other area of the healthcare facility, in which it is currently located.

In some embodiments, patient support apparatus 20 may be configured to determine its orientation and location within a given room or area of a healthcare facility, and tool 400 may be configured to communicate with patient support apparatus 20 and/or locator unit 60 in such a manner that tool 400 is able to determine its relative position and orientation within the same room or area. Using this information, controller 410 of tool 400 may then use locator unit 60, patient support apparatus 20, and/or its own UWB transceiver 412 to determine the location and orientation of any other UWB devices within the room or area, and to subsequently display them on screen 500. In some such embodiments, tool 400 and/or patient support apparatus 20 may be configured to determine their relative position/orientation within a room or area of a healthcare facility in any of the manners disclosed in commonly assigned U.S. provisional patent application Ser. No. 63/597,412 filed Nov. 9, 2023, by inventors Michael W. Graves et al. and entitled PATIENT SUPPORT APPARATUS WITH ENVIRONMENTAL INTERACTION, the complete disclosure of which is incorporated herein by reference.

Figure 8:
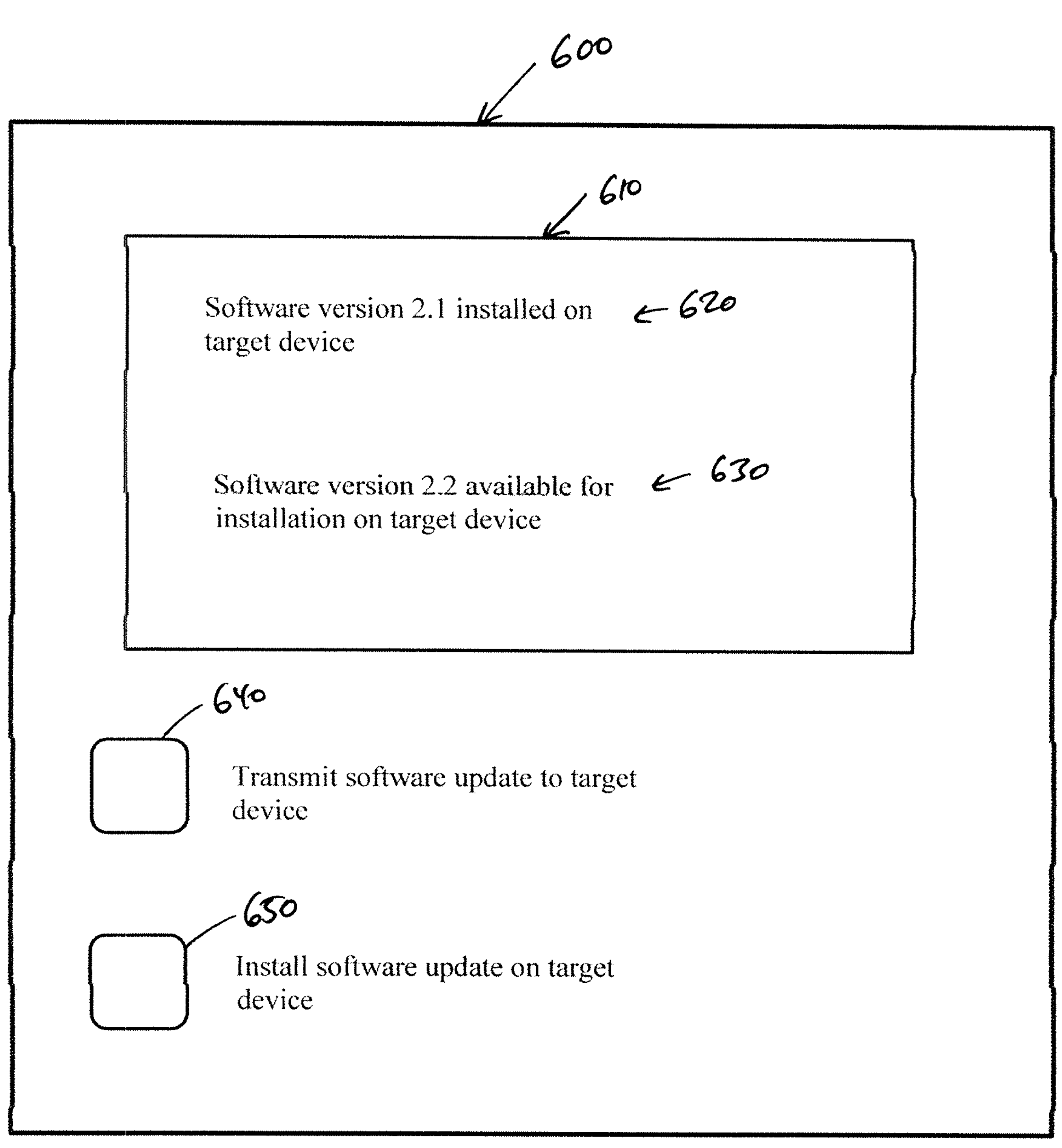
FIG. 8 is an example of a software update screen that may be displayed upon a display of the portable communication tool and/or a display in communication with the portable communication tool.

In those embodiments of tool 400 that are configured to install software updates on a target device (e.g. patient support apparatus 20, locator unit 60, and/or UWB device 100), tool 400 may be configured to display a software update screen, such as the software update screen 600 of FIG. 8. It will be understood, of course, that tool 400 may be configured to display a software update screen that varies from what is shown in FIG. 8, and such variations may additionally, and/or alternatively, include other software update information. Controller 410 of tool 400 is configured to display such software update information (e.g. screen 600) on display 404 and/or display 404*a*. In some embodiments, tool 400 may be configured to display screen 600 on still other displays (e.g. display 52 of patient support apparatus 20).

Software update screen 600 includes a status window 610, a currently installed software descriptor 620, a software update descriptor 630, a transmit software control 640, and an installation control 650. Status window 610 includes descriptors 620 and 630. Descriptor 620 informs the user of tool 400 what the current software version is that is installed on the target device (e.g. patient support apparatus 20, locator unit 60, and/or UWB device 100). Descriptor 630 informs the user of tool 400 what the most recent software version is that is available for the target device. Control 640, when activated by the user, transmits the latest software version (identified by descriptor 630) to the target device. Control 650, when activated by the user, commands the target device, after having received the updated software (via the prior activation of control 640) to install the latest software. In some embodiments, tool 400 transmits the software update and/or commands to the target device using UWB transceiver 412, while in other embodiments, tool 400 may transmit the software update and/or commands using another transceiver (e.g. Bluetooth transceiver 414).

Controller 410 of portable tool 400 is configured to send a message to the target device querying the device for its currently installed software version. When the target device responds with the software version currently installed thereon, controller 410 displays this information in descriptor 620 of window 610. For some target devices, there may be more than one piece of software installed thereon, in which case controller 410 queries the target device for the current versions of all of the different pieces of software installed thereon. After receiving a response from this query, tool 400 displays the currently installed software as part of descriptor 620.

In some embodiments, controller 410 of portable tool 400 is adapted to communicate with a computer network, such as network 80 and/or another network. More specifically, controller 410 is adapted to communicate with a server, such as patient support apparatus server 84 and/or remote server 86 that informs controller 410 of the most up-to-date software versions for one or more target devices. After receiving this information from the appropriate server, controller 410 displays the currently available software version in the descriptor 630 section of window 610.

In some embodiments, the target device sends a message to tool 400 prior to receiving a software update (via control 640) and/or prior to installation of the latest software update (via control 650). In such embodiments, the target device, prior to receiving a software update, may check to see if the tool 400 is within a threshold distance of the target device prior to allowing tool 400 to send the software update to the target device. Additionally, or alternatively, prior to installing a received software update, the target device may check to see that the target device is in an acceptable state to install the software update. The target device (e.g. locator unit 60, patient support apparatus 20, and/or another UWB device 100) may therefore perform a first check prior to receiving a software update and a second check prior to installing a software update. If the first check fails, controller 410 may send a message to tool 400 indicating that it will not allow receipt of a software update from tool 400. If the second check fails, controller 410 may send a message to tool 400 indicating that it will not install a software update at the current time. Both of these situations are discussed further below.

When the target device checks to see if it will allow receipt of a software update, it uses its UWB transceiver 158 to range with one or more of the UWB transceivers 412 of portable tool 400. After ranging and determining the distance between itself and tool 400, the controller of the target device (e.g. 156, 140, 112) checks to see if the distance is less than an allowable threshold. If the distance is less than the allowable threshold, then the target device accepts the software update. If the distance is more than the allowable threshold, then the target device does not accept the software update. In some embodiments, the target device sends a message to the portable tool 400 informing it of whether it will accept the software update or not (i.e. whether tool 400 is within the threshold distance). If the tool 400 is not within the threshold distance, the target device may command tool 400 to disable control 640, thereby preventing tool 400 from transmitting the software to the target device. Alternatively, or additionally, the target device may disallow, or not accept, the software update should it be attempted, thereby preventing the software update from being transferred, or installed, on the target device.

The threshold distance may be chosen in a wide variety of different manners. In general, the threshold distance is chosen so as to force the portable tool 400 to be within viewing range of the target device when the software update is transferred from the portable tool 400 to the target device. In this manner, the target device is adapted to prevent software from being sent to it that comes from a remote location (i.e. one that is not within viewing distance of the target device). This helps prevent unauthorized software from being installed on the target device. In some embodiments, the target distance may be on the order of 10 meters, although in other embodiments, it may be either less than, or more than this. Further, the target distance may be variable and/or chosen based upon the particular environment in which the target device is operating and/or one or more specific characteristics of the target device and/or tool 400.

Typically, after receiving a software update, the target device must be commanded to actually install the software update. Often this installation process can be performed by using a user interface of the target device itself (e.g. using one or more control panels 54 of patient support apparatus 20). However, in some embodiments, portable tool 400 is configured to allow the user to utilize the tool 400 to remotely install the updated software. Portable tool 400 sends a command to the target device to install the software update in response to a user activating control 650 (FIG. 8). As was alluded to previously, in some embodiments, the target device may automatically check to see if it is currently in a state that allows a software installation to take place or not. If it is in a state in which a software installation is not possible or desirable, the target device may ignore the command sent from tool 400 and/or it may send a message to portable tool 400 instructing it to disable control 650, thereby preventing tool 400 from being able to install a software update on the target device. If the target device is in a state in which a software installation is possible, the target device will react to the command from portable tool 400 (in response to control 650 being activated) by proceeding to install the updated software.

In general, the conditions which will put a target device into a first state (allow software installation) or a second state (disallow software installation) may vary for the particular device. In some embodiments of patient support apparatus 20, controller 140 of patient support apparatus 20 may be configured to prevent a software installation (i.e. be in the second state) in response to any one or more of the following conditions being true: (a) exit detection system 136 is armed; (b) scale system 144 detects a patient weight on patient support apparatus 20; and/or (c) monitoring system 138 is armed. Still other conditions may prevent controller 140 from allowing a software installation. If all of such conditions are false, then controller 140 may put patient support apparatus 20 in the first state and allow a software installation. In some embodiments, if controller 140 determines that patient support apparatus 20 is in a state in which it will not allow a software installation, it sends a message to portable tool 400 informing tool 400 of this fact and tool 400 reacts by disabling control 650. In such situations, controller 410 of tool 400 may display a message, or other indication, informing the user that control 650 is currently disabled. Controller 140 may also be configured to send a similar message to tool 400 when patient support apparatus 20 is in the first state.

In some embodiments of patient support apparatus 20, controller 140 is configured to prevent software from being installed when it is in the second state, regardless of whether the software was provided by tool 400 and/or regardless of whether the user tries to use control 650 to install the software, or a control onboard patient support apparatus 20. In other words, in some embodiments, when controller 140 tells tool 400 to disable control 650, controller 140 may also disable any controls onboard patient support apparatus 20 itself that would otherwise enable a user to install the software on patient support apparatus 20. In this manner, no software can be installed on patient support apparatus 20 while it is in the second state, regardless of whether a remote installation control (e.g. control 650) or a local installation control (not shown) is used.

In some embodiments, patient support apparatus 20, locator unit 60, and/or one or more UWB devices 100 are configured to only respond to portable tool 400 (for software updates and/or for other purposes) if portable tool 400 supplies them with a digital certificate (e.g. a public key certificate or identity certificate) that authenticates that portable tool 400 is a properly authorized device for communicating with patient support apparatus 20, locator unit 60, and/or the UWB device 100. Portable tool 400 may therefore be configured to include an authentic digital certificate and to transmit it to the device(s) it is in communication with in order to be able to properly communicate with them.

Portable tool 400, in some embodiments, is configured to command one or more of the target devices (e.g. locator unit 60, patient support apparatus 20, and/or a UWB device 100) to take one or more measurements of known distances using one or more of their respective UWB transceivers 126, 132, and/or 158). In such embodiments, the distances that are measured are known, and controller 410 is configured to compare the known distances to the measured distances. If they differ by more than a threshold, this is an indication that one or more of the UWB transceivers may be malfunctioning and/or that some aspect of the target device is not functioning properly. If they do not differ by more than the threshold, this is an indication that the one or more UWB transceivers are functioning properly and/or that the target device itself is functioning properly.

For example, in some embodiments, portable tool 400 may be configured to send a command to patient support apparatus 20 instructing controller 140 to take one or more of the distance measurements D1, D2, D3, D4, D5, and/or D6, as shown in FIG. 9. Such distance measurements are taken through ranging sessions between the different UWB transceivers 132 of patient support apparatus 20. Stored within memory 134 of patient support apparatus 20 are values representing the known distances D1-D6. These values are stored during the manufacture of patient support apparatus 20 and may be based upon a physical measurement of the distances D1-D6 (as opposed to a UWB measurement). After taking the UWB measurements of any one or more of distances D1-D6, controller 140 either compares these distances to the known distances stored in memory 134 or sends both the UWB-measured and known distances to portable tool 400 for comparison. In either situation, the UWB-measured distances are compared to the known distances and, if they differ by more than a threshold, portable tool 400 and/or controller 140 issue a notification to the user. The notification may comprise an audio and/or visual notification, and/or it may comprise sending a message to a remote location.

The threshold distance used for comparing the UWB-measured distances between UWB transceivers 132 and the known distances between UWB transceivers 132 is chosen such that it is greater than the typical accuracy range of UWB transceivers 132. In other words, the threshold distance is chosen such that it is more than the expected amount of variance of the UWB transceivers 132, thereby ensuring that if the threshold distance is exceeded, this is likely an indication that the UWB transceivers 132 are not operating properly, in which case a notification is provided to the user.

In some embodiments, if controller 140 and/or tool 400 detect that one or more of UWB-measured distances D1-D6 differ from their known values by more than the aforementioned threshold, controller 140 and/or tool 400 may be configured to automatically take one or more steps to determine which UWB transceivers 132 may be malfunctioning. In such embodiments, controller 140 may look at all six of the UWB-measured distances D1-D6 and see which UWB transceiver(s) 132 may be in common with the measurements that differ from the known values by more than the threshold. For example, if the UWB-measured distances D1, D4, and D5 all differ by more than the threshold from their known values, and none of distances D2, D3, or D6 differ by more than the threshold from their known values, this is an indicator that it is likely that the UWB transceiver 132 in the upper left corner of the patient support apparatus 20 shown in FIG. 9 is malfunctioning because that particular UWB transceiver 132 is the only one in common with the inaccurate UWB-measured distances D1, D4, and D5 (and because that particular UWB transceiver 132 is not utilized for distances D2, D3, and D6).

In some embodiments, locator unit 60 and/or one or more UWB devices 100 may include multiple UWB transceivers 126 and/or 158. In such embodiments, portable tool 400 may be configured to include a control that allows a user to send a command to these devices (60, 100) instructing the device to make a UWB-measurement of the distances between their UWB transceivers, and to then compare the UWB-measured distance to the known distance in the same manner discussed above. For example, tool 400 may be configured to allow a user to send a command to locator unit **60*a* instructing it to use its UWB transceivers 126 to measure the distance D7. Locator unit 60*a* includes within its memory a known value of the distance D7. Controller 112 and/or controller 410 of tool 400 compares the UWB-measured distance D7 to the known value of D7 and, if it differs by more than a threshold, tool 400 and/or locator unit 60 issues a notification. The notification may be the same or similar to the notifications discussed above for patient support apparatus 20. Locator unit 60*a* may be the same as locator unit 60, but include an extra one or more UWB transceivers 126**.

In some embodiments, portable tool 400 may be configured to allow a user to instruct a first device to take UWB-measurements of one or more known distances between UWB transceivers that are positioned onboard a second device (and to them compare them to the known distances to see if there differ by more than the corresponding threshold). For example, in some embodiments, portable tool 400 may allow a user to command patient support apparatus 20 to use its UWB transceivers 132 to measure the distance D7 between UWB transceivers 126 of locator unit **60*a*. This distance is measured by ranging between UWB transceivers 132 and 126. After the distance D7 is determined by controller 140, controller 140 compares the UWB-measured distance D7 to the known value of D7 and, if it differs by more than the threshold, it issues a notification. Alternatively, controller 140 may forward the UWB-measured distance D7 to tool 400, and locator unit 60*a* may forward the known value of D7 to tool 400, and controller 410** may then compare the two value and issue a notification if they differ by more than the threshold.

It will be understood that, in addition to, or in lieu of, patient support apparatus 20 measuring the distance between multiple UWB transceivers of another locator unit 60, patient support apparatus 20 may measure the known distances between two or more UWB transceivers 158 that are positioned on a UWB device. Similarly, a locator unit **60*a* may be instructed by tool 400 to measure any of the distances D1-D6 and/or a distance between any UWB devices 100 that include multiple UWB transceivers 158. Similarly, any UWB device 100 that includes multiple UWB transceivers 158 may be instructed by portable tool 400 to measure the distances between multiple UWB transceivers that are positioned onboard patient support apparatus 20, locator unit 60*a*, and/or another UWB device 100**.

In some embodiments, controller 140 is configured to make UWB-measurements of distances D1-D6, compare them to the threshold, and issue a notification if they differ by more than the threshold, in response to one or more other triggers besides a command from portable tool 400. In such embodiments, controller 140 may be configured to make one or more UWB-measurements of distances D1-D6 and compare them to their known values in response to any one or more of the following: (a) the passage of a set amount of time, (b) a user activating a control onboard patient support apparatus 20, (c) an event detected by one or more sensors onboard patient support apparatus 20 (e.g. the arming/disarming of any of scale system 144, monitoring system 138, exit detection system 136, and/or other events); (d) a command received from patient support apparatus server 84 and/or remote server 86; and/or (e) other triggers. As noted, if the measured UWB-distance differs from the known value, tool 400 (and/or the device 20, 60, or 100 to which the UWB-distance measurement applies) may issue a notification to the user informing them of the discrepancy between the measured and known distances. In this manner, a service technician may be notified that one or more of the UWB transceivers may be malfunctioning.

In some embodiments, tool 400 may be configured to instruct UWB transceivers that are not part of the same device, but that are positioned a known distance from each other, to measure their distances to see if the measured distances differ from their known distances by more than the threshold. For example, in some embodiments, fixed locator units 60 and/or other UWB tags may be placed at known locations on walls, ceilings, or on other structures. In response to a command from tool 400, the UWB tags and/or fixed locator units 60 may measure the known distances between themselves and report the UWB measurements to portable tool 400. Tool 400, as noted, then compares the measured distances to the known distances and issues a notification if they differ by more than the threshold.

From the foregoing description, it can be seen that tool 400 may be used to identify nearby UWB devices (e.g. locator units 60, patient support apparatuses 20, and/or other UWB devices 100) and present the software update availability status for the identified devices. A service technician can then evaluate the reading of the devices to receive the update and to thereafter initiate the software update. Permissions can be set for different user roles. A map of devices in their physical location can be displayed and/or otherwise made available if there are more than one UWB device to be updated. Additional security features such as certificates can be implemented. The UWB channel itself, or another channel, can be used to transmit the updated software.

It will be understood by those skilled in the art that the use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A portable tool for communicating with a patient support apparatus, the tool comprising:
- a housing;
- a transceiver for communicating with a computer;
- a first ultra-wideband (UWB) transceiver adapted to communicate with a second UWB transceiver incorporated into the patient support apparatus; and
- a controller adapted to perform the following:
- (a) use the first UWB transceiver to obtain an identifier from the second UWB transceiver onboard the patient support apparatus;
- (b) determine an internal location of the second UWB transceiver within the patient support apparatus based on the identifier; and
- (c) forward the identifier and the internal location of the second UWB transceiver to the transceiver for display on the computer.

2. The tool of claim 1 wherein the controller is further adapted to determine a distance between the first UWB transceiver and the second UWB transceiver by using the first UWB transceiver to range with the second UWB transceiver using ultra-wideband.

3. The tool of claim 2 wherein the controller is further adapted to forward the distance to the transceiver for display on the computer.

4. The tool of claim 1 wherein the controller is further adapted to measure a quality of UWB signals sent by the second UWB transceiver and detected by the first UWB transceiver.

5. The tool of claim 4 wherein the controller is further adapted to forward the measurement of quality to the transceiver for display on the computer.

6. The tool of claim 1 wherein the controller is further adapted to use the first UWB transceiver to retrieve error codes from the second UWB transceiver.

7. The tool of claim 6 wherein the controller is further adapted to forward the error codes to the transceiver for display on the computer.

8. A portable tool for communicating with at least one of a patient support apparatus or locator unit mounted at a fixed location within a healthcare facility, the tool comprising:
- a housing;
- a transceiver for communicating with a computer;
- a first ultra-wideband (UWB) transceiver adapted to communicate with a second UWB transceiver; and
- a controller adapted to perform the following:
- (a) use the first UWB transceiver to obtain an identifier from the second UWB transceiver;
- (b) determine whether the second UWB transceiver is onboard the patient support apparatus or onboard the locator unit based on the identifier;
- (c) determine a model of the patient support apparatus or locator unit from the identifier; and
- (d) forward data indicating the model and whether the second UWB transceiver is onboard the patient support apparatus or onboard the locator unit to the transceiver for display on the computer.

9. The tool of claim 8 wherein the controller is further adapted to determine a distance between the first UWB transceiver and the second UWB transceiver by using the first UWB transceiver to range with the second UWB transceiver using ultra-wideband.

10. The tool of claim 9 wherein the controller is further adapted to forward the distance to the transceiver for display on the computer.

11. The tool of claim 8 wherein the controller is further adapted to measure a quality of UWB signals sent by the second UWB transceiver and detected by the first UWB transceiver.

12. The tool of claim 11 wherein the controller is further adapted to forward the measurement of quality to the transceiver for display on the computer.

13. The tool of claim 8 wherein the controller is further adapted to use the first UWB transceiver to retrieve error codes from the second UWB transceiver.

14. A portable tool for communicating a software update to a device, the tool comprising:
- a housing;
- a first ultra-wideband (UWB) transceiver adapted to communicate with a second UWB transceiver positioned on the device;
- a software update control adapted to send updated software to the device when activated by a user; and
- a controller adapted to perform the following:
- (a) transmit a first query from the first UWB transceiver to the second UWB transceiver requesting a software identifier indicating a current version of software on the device;
- (b) determine a distance between the first UWB transceiver and the second UWB transceiver;
- (c) enable the software update control if the distance between the first UWB transceiver and the second UWB transceiver is less than a threshold; and
- (d) disable the software update control if the distance between the first UWB transceiver and the second UWB transceiver is more than the threshold.

15. The portable tool of claim 14 further comprising a software installation control that, when activated by a user, is adapted to command the device to install the updated software; and
- wherein the controller is further adapted to perform the following:
- (e) transmit a second query to the device requesting an indication of whether the device is in a first state in which the device is able to install the updated software or a second state in which the device is not able to install the updated software;
- (f) enable the software installation control if the device is in the first state; and
- (g) disable the software installation control if the device is in the second state.

16. The portable tool of claim 15 wherein the device is a patient support apparatus.

17. The portable tool of claim 14 wherein the device is a locator unit adapted to provide a wireless signal indicative of a location of the locator unit.

18. The portable tool of claim 14 wherein the controller is further adapted to send a command to the device instructing the device to use the second UWB transceiver to determine a measured second distance between the second UWB transceiver and a third UWB transceiver positioned onboard the device, wherein the third UWB transceiver is positioned at a known second distance away from the second UWB transceiver.

19. The portable tool of claim 18 wherein the controller is adapted to determine a difference between the measured second distance and the known second distance and issue a notification if the difference exceeds a second threshold.

20. The portable tool of claim 14 wherein the controller is further adapted to send a command to the device instructing the device to use the second UWB transceiver to determine a measured second distance between a third UWB transceiver and a fourth UWB transceiver, wherein the third UWB transceiver is positioned at a known second distance away from the fourth UWB transceiver.

* * * * *